US006673602B1

(12) United States Patent
Spear et al.

(10) Patent No.: US 6,673,602 B1
(45) Date of Patent: Jan. 6, 2004

(54) HERPES SIMPLEX VIRUS AMPLICON VECTOR TARGETING SYSTEM AND METHOD OF USING SAME

(75) Inventors: Matthew A. Spear, San Diego, CA (US); Xandra O. Breakefield, Newton, MA (US)

(73) Assignees: The General Hospital Corporation, Boston, MA (US); The Regents of the University of California, Oakland, CA (US)

( * ) Notice: Subject to any disclaimer, the term of this patent is extended or adjusted under 35 U.S.C. 154(b) by 67 days.

(21) Appl. No.: 09/592,537

(22) Filed: Jun. 12, 2000

Related U.S. Application Data
(60) Provisional application No. 60/138,963, filed on Jun. 11, 1999.

(51) Int. Cl.$^7$ .......................... C12N 15/00; C12Q 1/00; C12P 21/06; A61K 39/00; A61K 39/12
(52) U.S. Cl. ................. 435/320.1; 435/5; 435/69.1; 424/199.1; 424/205.1; 424/231.1
(58) Field of Search .................... 435/320.1, 235.1, 435/456, 5, 69.1; 514/44; 424/231.1, 199.1, 205.1

(56) References Cited

U.S. PATENT DOCUMENTS

| | | | |
|---|---|---|---|
| 5,501,979 A | 3/1996 | Geller et al. | 435/320.1 |
| 5,529,774 A | 6/1996 | Barba et al. | 424/93.21 |
| 5,601,818 A | 2/1997 | Freeman et al. | 424/93.21 |
| 5,631,236 A | 5/1997 | Woo et al. | 514/44 |
| 5,670,488 A | 9/1997 | Gregory et al. | 514/44 |
| 5,688,773 A | 11/1997 | Chiocca et al. | 514/44 |
| 5,691,177 A | 11/1997 | Guber et al. | 435/172.3 |
| 5,763,217 A | 6/1998 | Cynader et al. | 435/69.1 |
| 5,869,331 A | 2/1999 | Dornburg | 435/320.1 |

FOREIGN PATENT DOCUMENTS

| | | |
|---|---|---|
| WO | WO 90/02809 | 3/1990 |
| WO | WO 97/05263 | 2/1997 |
| WO | WO 99/06583 A1 | 2/1999 |

OTHER PUBLICATIONS

Rudinger, "Characterization of the amino acids as components of a peptide hormone sequence", pp. 1–7, In Peptide Hormones, Parsons (ed.), University Park Press, Baltimore, Jun. 1976.*
Spear, "Targeting gene therapy vectors to CNS malignancies", J. Neurovirol., 4(2):133–147, Apr. 1998.*
Anderson, "Human gene therapy", Nature, 392(Supp.):25–30, Apr. 1998.*
Verma et al., "Gene therapy—promises, problems and prospects", Nature, 389:239–242, Sep. 1997.*
Laquerre, S., et al., "Gene–transfer Tool: Herpes Simplex Virus Vectors," in The Development of Human Gene TherapyFriedman, T., ed., Cold Spring Harbor Laboratory Press, Cold Spring Harbor, NY, pp. 173–208 (1999).

Wang, S., and Vos, J.–M., "A Hybrid Herpesvirus Infections Vector Based on Epstein–Barr virus and Herpes Simplex Virus Type 1 for Gene Transfer into Human Cells In Vitro and In Vivo," J. Virol. 70:8422–8430 (1996).
Abe, M., and Kufe, D., "Characterization of cis–acting elements regulating transcription of the human DF3 breast carcinoma–associated antigen (MUC1) gene," Proc. Natl. Acad. Sci. USA 90:282–286 (1993).
Arbuthnot, P., et al., "Hepatoma Cell–Specific Expression of a Retrovirally Trnasferred Gene Is Achieved by α–Fetoprotein but Not Insulinlike Growth Factor II Regulatory Sequences," Hepatology 22:1788–1796 (1995).
Bilbao, G., et al., "Adenoviral/retroviral vector chimeras: a novel strategy to achieve high–efficiency stable transduction in vivo," FASEB J. 11:624–634 (1997).
Blankenstein, T., et al., "Tumor Suppression after Tumor Cell–targeted Tumor Necrosis Factor α Gene Transfer," J. Exp. Med. 173:1047–1052 (1991).
Bour, S., et al., "The Human Immunodeficiency Virus Type 1 (HIV–1) CD4 Receptor and Its Central Role in Promotion of HIV–1 Infection," Microbiol. Rev. 59:63–93 (1995).
Breakefield, X.O., et al., "Herpes Simplex Virus Vectors for Tumor Therapy," in The Internet Book of Gene Therapy: Cancer Gene Therapeutics, R.E. Sobol and K.J. Scanlon, eds., Appleton and Lange, Stamford, CT, pp. 41–56 (1995).
Chase, M., et al., "An oncolytic viral mutant that delivers the CYP281 transgene and augments cyclophosphamide chemotherapy," Nature Biotechnol. 16:44–448 (1998).
Chen, L., et al., "Breast Cancer Selective Gene Expression and Therapy Mediated by Recombinant Adenoviruses Containing the DF3/MUC1 Promoter," J. Clin. Invest. 96:2775–2782 (1995).
Chung, R.Y., et al., B–myb Promoter Retargeting of Herpes Simplex Virus γ34.5 Gene–Mediated Virulence Toward Tumor and Cycling Cells, J. Virol. 73:7556–7564 (1999).
Clary, B.M., et al., "Transcriptional Targeting for Cancer Gene Therapy," Surg. Oncol. Clin. N. Am. 7:565–574 (1998).
Coll–Fresno, P.M., et al., "Cytotoxic activity of a diptheria toxin/FGF6 milotoxin on human tumour cell lines," Oncogene 14:243–247 (1997).

(List continued on next page.)

Primary Examiner—Deborah Crouch
Assistant Examiner—Joseph Woitach
(74) Attorney, Agent, or Firm—Sterne, Kessler, Goldstein & Fox, P.L.L.C.

(57) ABSTRACT

The present invention relates to herpes simplex virus (HSV) amplicon vectors, and in particular, HSV-1 amplicon vectors, which have been genetically modified and used alone or with consequent genetically modified HSV virus, to target a selected cell type, such as neoplastic cells. The present invention also relates to methods of using such vectors to target a cell, in order to treat a pathologic condition, such as cancer.

40 Claims, 8 Drawing Sheets

OTHER PUBLICATIONS

Colombo, M.P., et al., "Immunotherapy I: Cytokine gene transfer strategies," *Cancer Metastasis Rev.* 16:421–432 (1997).

Cunningham, C., and Davison, A.J., "A Cosmid–Based System for Constructing Mutants of Herpes Simplex Virus Type 1," *Virology* 197:116–124 (1993).

Dachs, G.U., et al., "Targeting Gene Therapy to Cancer: A Review," *Oncol. Res.* 9:313–325 (1997).

During, M.J., et al., "Long–Term Behavioral Recovery in Parkinsonian Rats by an HSV Vector Expressing Tyrosine Hydroxylase," *Science* 266:1399–1403 (1994).

Fraefel, C., et al., "Gene Transfer into Hepatocytes Mediated by Helper Virus–Free HSV/AAV Hybrid Vectors," *Mol. Med. New York* 3:813–825 (1997).

Fraefel, C., et al., "Helper Virus–Free Transfer of Herpes Simplex Virus Type 1 Plasmid Vectors into Neural Cells," *J. Virol.* 70:7190–7197 (1996).

Geller, A.I., and Breakefield, X.O., "A Defective HSV–1 Vector Expresses *Escherichia coli* β–Galactosidase in Cultured Peripheral Neurons," *Science* 241:1667–1669 (1988).

Geller, A.I., et al., "An efficient deletion mutant packaging system for defective herpes simplex virus vectors: Potential applications to human gene therapy and neuronal physiology," *Proc. Natl. Acad. Sci. USA* 87:8950–8954 (1990).

Glorioso, J.C., et al., "Herpes Simplex Virus as a Gene–Delivery Vector for the Central Nervous System," in *Viral Vectors: Gene Therapy and Neuroscience Applications*, M.G. Kaplitt and A.D. Loewy, eds., Academic Press, New York, pp. 1–23 (1995).

Glorioso, J.C., et al., "Development and Application of Herpes Simplex Virus Vectors for Human Gene Therapy," *Ann. Rev. Microbiol.* 49:675–710 (1995).

Goldstein, D.J., and Weller, S.K., "Factor(s) Present in Herpes Simplex Virus Type 1–infected Cells Can Compensate for the Loss of the Large Subunit of the Viral Ribonucleotide Reductase: Characterization of an ICP6 Deletion Mutant," *Virology* 166:41–51 (1988).

Gonzalez, R., et al., "Increased gene transfer in acute myeloid leukemic cells by an adenovirus vector containing a modified fiber protein," *Gene Ther.* 6:314–320 (1999).

Herold, B.C., et al., "Glycoprotein C–independent binding of herpes simplex virus to cells requires cell surface heparen sulphate and glycoprotein B," *J. Gen. Virol.* 75:1211–1222 (1994).

Herold, B.C., et al., "Glycoprotein C of Herpes Simplex Virus Type 1 Plays a Principal Role in the Adsorption of Virus to Cells and in Infectivity," *J. Virol.* 65:1090–1098 (1991).

Hollywood, D.P., and Hurst, H.C., "A novel transcription factor, OB2–1, is required for overexpression of the proto–oncogene c–erbB–2 in mammary tumour lines," *EMBO J.* 12:2369–2375 (1993).

Hwang, J.J., et al., "Novel Retroviral Vector Transferring a Suicide Gene and a Selectable Marker Gene with Enhanced Gene Expression by Using a Tetracycline–Responsive Expression System," *J. Virol.* 70:8138–8141 (1996).

Jacoby, D.R., et al., "Hybrid vectors: a new generation of virus–based vectors designed to control the cellular fate of delivered genes," *Gene Ther.* 4:1281–1283 (1997).

Kasahara, N., et al., "Tissue–Specific Targeting of Retroviral Vectors Through Ligand–Receptor Interactions," *Science* 266:1373–1376 (1994).

Kramm, C.M., et al., "Gene Therapy for Brain Tumors," *Brain Pathology* 5:345–381 (1995).

Krisky, D.M., et al., "Development of herpes simplex virus replication–defective multigene vectors for combination gene therapy applications," *Gene Ther.* 5:1517–1530 (1998).

Laquerre, S., et al., "Recombinant Herpes Simplex Virus Type 1 Engineered for Targeted Binding to Erythropoietin Receptor–Bearing Cells," *J. Virol.* 72:9683–9697 (1998).

Latchman, D.S., "Herpes Simplex Virus Vectors for Gene Therapy," *Mol. Biotechnol.* 2:179–195 (1994).

Lim, F., et al., "Generation of High–Titer Defective HSV–1 Vectors Using an IE 2 Deletion Mutant and Quantitative Study of Expression in Cultured Cortical Cells," *BioTechniques* 20:460–469 (1996).

Liu, H., et al., "Monoclonal Antibodies to the Extracellular Domain of Prostate–Specific Membrane Antigen also React with Tumor Vascular Endothelium," *Cancer Res.* 57:3629–3634 (1997).

Lorimer, I., et al., "Recombinant immunotoxins specific for a mutant epidermal growth factor receptor: Targeting with a single chain antibody variable domain isolated by phage display," *Proc. Natl. Acad. Sci. USA* 93:14815–14820 (1996).

Lundwall, A., "Characterization of the gene for Prostate–specific antigen, a human glandular kallikrein," *Biochem. Biophys. Res. Commun.* 161:1151–1159 (1989).

Massie, B., et al., "Inducible Overexpression of a Toxic Protein by an Adenovirus Vector with a Tetracycline–Regulatable Expression Cassette," *J. Virol.* 72:2289–2296 (1998).

Miller, N., and Whelan, J., "Progress in Transcriptionally Targeted and Regulatable Vectors for Genetic Therapy," *Hum. Gene Ther.* 8:803–815 (1997).

Missale, C., et al., "Dopamine Receptors: From Structure to Function," *Physiol. Rev.* 78:189–225 (1998).

O'Neil, K., and Hoess, R., "Phage display: protein engineering by directed evolution," *Curr. Opin. Struct. Biol.* 5:443–449 (1995).

Osaki, T., et al., "Gene Therapy for Carcinoembryonic Antigen–Producing Human Lung Cancer Cells by Cell Type–Specific Expression of Herpes Simplex Virus Thymidine Kinase Gene," *Cancer Res.* 54:5258–5261 (1994).

Pechan, P., et al., "Combined HSV–1 Recombinant and Amplicon Piggyback Vectors: Replication–Competent and Defective Forms, and Therapeutic Efficacy for Experimental Gliomas," *J. Gene Med.* 1:176–185 (1999).

Puri, R.K., et al., "Human Neurological Cancer Cells Express Interleukin–4 (IL–4) Receptors Which are Targets for the Toxic Effects of IL4–Pseudomonas Exotoxin Chimeric Protein," *Int. J. Cancer* 58:574–581 (1994).

Puri, R.K., et al., "Interleukin–4 receptor (IL–4R) directed targeting of a circular permuted IL4–pseudomonas exotoxin (CP–IL4–toxin) to human breast carcinoma cells," *Proc. Am. Assoc. Cancer Res. Ann. Meet.* 37:417 Abstract #284B (1996).

Robbins, P.D., et al., "Viral vectors for gene therapy," *Trends Biotechnol.* 16:35–40 (1998).

Saeki, Y., et al., "Herpes Simplex Virus Type 1 DNA Amplified as Bacterial Artificial Chromosome in *Escherichia coli*: Rescue of Replication–Competent Virus Progeny and Packaging of Amplicon Vectors," *Hum. Gene Ther.* 9:2787–2794 (1998).

Shaughnessy, E., et al., "Parvoviral Vectors for the Gene Therapy of Cancer," *Semin. Oncol.* 23:159–171 (1996).

Sheng, M., and Pak, D.T.S., "Ligand–Gated Ion Channel Interactions with Cytoskeletal and Signaling Proteins," *Ann. Rev. Physiol.* 62:755–778 (2000).

Sodee, D.B., et al., "Preliminary Imaging Results Using In–111 Labeled CYT–356 (Prostascint™) in the Detection of Recurrent Prostate Cancer," *Clin. Nucl. Med.* 21:759–767 (1996).

Spaete R.R., and Frenkel, N., The Herpes Simplex Virus Amplicon: A New Eucaryotic Defective–Virus Cloning-Amplifying Vector, *Cell 30*:295–304 (1982).

Spear, M.A., "Gene Therapy of Gliomas: Receptor and Transcriptional Targeting," *Anticancer Res.* 18:3223–3231 (1998).

Spear, M.A., "Efficient DNA Subcloning Through Selective Restriction Endonuclease Digestion," *BioTechniques* 28:660–662, 664, 666 (Apr. 2000).

Spear, M.A., et al., "Phage Display Eptitopes Selected Against Viable Glioblastoma Cells for Insertion into an HSV–1 Amplicon Vector Targeting System," *Proc. Am. Assoc. Cancer Res.* 41:466 Abstract #2969 (Mar. 2000).

Spear, M.A., et al., "Cytotoxicity, apoptosis, and viral replication in tumor cells treated with oncolytic ribonucleotide reductase–defective herpes simplex type 1 virus (hrR3) combined with ionizing radiation," *Cancer Gene Ther.* 7:1051–1059 (Jul. 2000).

Sulkowski, E., "Purification of proteins by IMAC," *Trends in Biotechnol.* 3:1–7 (1985).

Sun, F., and Spear, M.A., "Novel HSV–1 amplicon vector targeting system allows generation of amplicon producer cell lines," *Cancer Gene Ther.* 6:S15 Abstract #P–57 (1999).

Tal–Singer, R., et al., "Interaction of Herpes Simplex Virus Glycoprotein gC with Mammalian Cell Surface Molecules," *J. Virol.* 69:4471–4483 (1995).

Trybala, E., et al., Localization of a functional site on herpes simplex virus type 1 glycoprotein C involved in binding to cell surface heparan sulphate, *J. Gen. Virol.* 75:743–752 (1994).

Vile, R.G., "Tumor–specific gene expression," *Semin. Cancer Biol.* 5:429–436 (1994).

Vile, R.G., and Hart, I.R., "Targeting of cytokine gene expression to malignant melanoma cells using tissue specific promoter sequences," *Ann. Oncol.* 5(*Suppl. 4*):S59–S65 (1994).

Walther, W., and Stein, U., "Cell type specific and inducible promoters for vectors in gene therapy as an approach for cell targeting," *J. Mol. Med.* 74:379–392 (1996).

Wikstrand, C.J., et al., "Monoclonal Antibodies Against EGFRvIII are Tumor Specific and React with Breast and Lung Carcinomas and Malignant Gliomas," *Cancer Res.* 55:3140–3148 (1995).

Wilson, J.M., "Vectors—shuttle vehicles for gene therapy," *Clin. Exp. Immunol.* 107(*Suppl. 1*):31–32 (1997).

Wolfe, J.H., et al., "Herpesvirus vector gene transfer and expression of β–glucuronidase in the central nervous system of MPS VII mice," *Nat. Genet.* 1:379–384 (1992).

WuDunn, D., and Spear, P.G., "Initial Interaction of Herpes Simplex Virus with Cells is Binding to Heparan Sulfate," *J. Virol.* 63:52–58 (1989).

Zaia, J.A., et al., "Status of Ribozyme and Antisense–Based Developmental Approaches for Anti–HIV–1 Therapy," *Ann. N.Y. Acad. Sci.* 660:95–106 (1992).

Zhang, J., et al., "Vectors for cancer gene therapy," *Cancer Metastasis Rev.* 15:385–401 (1996).

\* cited by examiner

FIG. 8B LacZ
FIG. 8A GFP

HERPES SIMPLEX VIRUS AMPLICON VECTOR TARGETING SYSTEM AND METHOD OF USING SAME

CROSS-REFERENCE TO RELATED APPLICATION

This application claims the benefit of U.S. Provisional Application No. 60/138,963, filed Jun. 11, 1999. The content of this application is relied upon and incorporated by reference in its entirety.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under grant number CA 69246, awarded by the National Cancer Institute. The U.S. Government has certain rights in this invention.

BACKGROUND OF THE INVENTION

1. Field of the Invention

The present invention relates generally to viral vectors useful for specifically targeting one or more selected cell types. More specifically, the present invention relates to herpes simplex virus (HSV) virions comprising HSV amplicon vectors or a mixture of HSV amplicon vectors and recombinant HSV vectors, which are modified to target and infect a selected cell type. The present invention also relates to methods of making such virions, as well as methods of using such virions to target a cell in order to treat a pathologic condition.

2. Related Art

Many pathologies have a genetic basis. For example, genes have been identified that, when expressed, prevent cells from becoming cancer cells. When a mutation occurs in such a tumor suppressor gene, the cell is released from its normal growth control and can give rise to a cancer in an individual. Many other diseases are also associated with genetic defects, including, for example, cystic fibrosis, hemophilia, sickle cell anemia, and Huntington's disease. More diseases having a genetic component are likely to be identified in the future.

Methods for treating such diseases often are not selective for the disease, or only moderate the symptoms associated with the disease. For example, chemotherapy often is used to treat cancer patients, particularly patients with disseminated disease. However, while chemotherapy can kill cancer cells, for example, due to their rapid growth rate, chemotherapeutic agents also kill normal cells such as intestinal cells and blood precursor cells, which, like cancer cells, have a rapid growth rate. In fact, treatments for cancer often are limited by the damage the treatment causes to the normal cells in a patient.

Gene therapy provides a means for selectively treating genetic diseases such as cancer by replacing the defective gene, for example, a mutated tumor suppressor gene, with a normal copy of the gene, or by introducing into the cancer cells a gene that, when expressed, results in a product that kills the cancer cells. The transfer of specific genes into cells through gene therapy paradigms offers almost unlimited potential for the treatment of human disease, most of which is yet unrealized. Gene-based therapies are now expanding into fields such as cardiovascular disease, autoimmune disease, and neurodegenerative disease. However, to be effective, gene therapy must be selective, i.e., the gene must be delivered to target cells that have the defect to be corrected, or the cells that are to be killed.

This is particularly true for the treatment of cancer, where the transgenes or vectors are usually intended to be toxic. Each cancer therapy currently in use (surgery, radiation, or chemotherapy) has its own mechanism and profile of selective elimination of tumor cells as opposed to normal cells, and thus provides a unique contribution to the therapeutic ratio. Therapies are often combined such that additive or synergistic toxicity to tumor cells is maximized, while toxicity to normal tissue is minimized. Cure is frequently not achieved because each modality first reaches a point at which toxicity to vital normal tissues is limiting and overlaps with other agents. This issue is also relevant to other non-cytotoxic therapeutic goals, in for which the inappropriate introduction of viral or therapeutic proteins and genes could still impair or alter the function of non-target cells.

Gene therapy requires the use of viral-based or non-viral-based vectors to carry the gene into the target cells. Often, however, the vectors are not selective for a particular cell type, but can be taken up by any cell the vector contacts. Viral vectors provide an advantage in that many viruses only infect one or a few different types of cells. However, the use of such viral vectors is limited, at best, to treating the particular cells the virus infects. Some viral vectors, however, actually infect a relatively broad spectrum of host cells.

An overview of viral vectors that have been used in gene therapy can be found in Wilson, J. M., *Clin. Exp. Immunol.* 107(Suppl. 1):31–32 (1997), Nakanishi, M., *Crit. Rev. Therapeu. Drug Carrier Systems* 12:263–310 (1995); Robbins, P. D., et al., *Trends Biotechnol.* 16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA (Vile, R. G., et al., *Br. Med Bull.* 51:12–30 (1995)) or DNA (Ali M., et al., *Gene Ther.* 1:367–384 (1994)).

Specific examples of viral vector systems that have been utilized include: retroviruses (Vile, R. G., supra; U.S. Pat. Nos. 5,741,486 and 5,763,242); adenoviruses (Heise, C. et al., *Nat. Med.* 3:639–645 (1997)); adenoviral/retroviral chimeras (Bilbao, G., et al., *FASEB J.* 11:624–634 (1997); adeno-associated viruses (Flotte, T. R. and Carter, B. J., *Gene Ther.* 2:357–362 (1995); U.S. Pat. No. 5,756,283); herpes simplex virus 1 or 2 (Latchman, D. S., *Mol. Biotechnol.* 2:179195 (1994); U.S. Pat. Nos. 5,501,979 and 5,763, 217; Chase, M., et al., *Nature Biotechnol.* 16:444–448 (1998)); parvovirus (Shaughnessy, E., et al., *Semin Oncol.* 23:159–171 (1996)); reticuloendotheliosis virus (Donburg, R., *Gene Therap.* 2:301–310 (1995)). Other viruses that can be used as vectors for gene delivery include poliovirus, papillomavirus, vaccinia virus, lentivirus, as well as hybrid or chimeric vectors incorporating favorable aspects of two or more viruses (Nakanishi, M., supra; Zhang, J., et al., supra; Jacoby, D. R., et al., *Gene Therapy* 4:1281–1283 (1997)).

General guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,529,774, and 5,601,818.

Most viruses, which most vectors are or resemble, use viral surface proteins that bind to specific cell surface molecules (receptors) as the primary means of initiating cellular attachment. Expression of the receptors on a single or limited range of cell types produces the tissue tropism seen with many viruses. This effect is frequently a major determinant in the disease syndrome produced. A separate domain of the binding protein, an associated protein, or a completely unrelated protein usually provides a subsequent and usually less specific membrane fusion or penetration function.

Since many of the commonly used viral vectors actually infect a relatively broad spectrum of host cells, and the non-viral vectors have almost no intrinsic selectivity, significant advantages can be obtained by targeting vector transduction to one or a few specific cell types. For example, targeting vector toxicity to tumor cells can provide a unique contribution to the therapeutic ratio of a combined modality cancer therapy regimen. Significant interest exists in increasing the specificity of vector infectivity by adding or altering receptor-binding moieties, thus increasing the transduction of tumor and tumor associated cells, while decreasing gene delivery to non-target cells.

This has been attempted by attaching or conjugating various receptor ligands and specific antibodies, as well as by recombinant modification of viral surface molecules, with binding domains from ligands or antibodies (for review, see, Spear, M. A., *Anticancer Research* 18:3223–3231 (1998)). For example, the Moloney murine leukemia virus (MMLV) gp70 envelope protein has been modified in a variety of ways and expressed in trans in packaging cell lines. Kasahara et al. inserted the receptor-binding domain of erythropoietin and achieved increased transduction of erythropoietin receptor-bearing human cells, including erythroid and erythroleukemia cell lines, and decreased transduction of cell lines not expressing erythropoietin receptors (Kasahara, N., et al., *Science* 266:1373–1375 (1991). Modifications have also been introduced into the fiber protein of adenovirus to increase infectivity (Gonzalez, R., et al., *Gene Ther.* 6:314–320 (1999).

Viral vectors based on herpes simplex virus (HSV), and especially HSV-1, have shown promise as potent gene delivery vehicles for several reasons: the virus has a very large genome and thus can accommodate large amounts of foreign DNA (greater than 50 kb), the virus can persist long-term in cells, and can efficiently infect many different cell types, including post-mitotic neural cells (Breakefield, X.O., et al., "Herpes Simplex Virus Vectors for Tumor Therapy," in *The Internet Book of Gene Therapy: Cancer Gene Therapeutics*, R. E. Sobol and K. J. Scanlon, eds., Appleton and Lange, Stamford, Conn., pp. 41–56 (1995); Glorioso, J. C., et al., "Herpes Simplex Virus as a Gene-Delivery Vector for the Central Nervous System," in *Viral Vectors: Gene Therapy and Neuroscience Applications*, M. G. Kaplitt and A. D. Loewy, eds., Academic Press, New York, pp. 1–23 (1995)).

Two types of HSV-1 vector systems are known: recombinant and amplicon. Each will be discussed in turn.

Recombinant HSV-1 vectors (Wolfe, J. H. et al., *Nat. Genet.* 1:379–384 (1992)) are created by inserting genes of interest directly into the 152 kb viral genome, thereby mutating one or more of the approximately 80 viral genes, and usually concomitantly reducing cytotoxicity.

HSV-1 amplicons are bacterial plasmids containing only about 1% of the 152 kb HSV-1 genome. Typically, they are packaged into infectious HSV-1 particles ("virions") using HSV-1 helper virus functions. HSV-1 amplicons contain: (i) a transgene cassette with a gene(s) of interest; (ii) sequences that allow plasmid propagation in *E. coli*, such as the origin of DNA replication colE1 and the ampicillin resistance gene; and (iii) non-coding elements of the HSV-1 genome, in particular an origin of DNA replication (ori) and a DNA cleavage/packaging signal (pac), to support replication and subsequent packaging of the amplicon DNA into virions in the presence of helper functions (Spaete, R. R. and Frenkel, N., *Cell* 30:295–304 (1982)). HSV amplicon vectors are one of the most versatile, most efficient, and least toxic, and have the largest transgene capacity of the currently available virus vectors. HSV-1 amplicon vectors can support some gene expression for up to one year in non-dividing cells (During, M. J., et al., *Science* 266:1399–1403 (1994)).

Because HSV-1 encodes many toxic functions, improvements on the amplicon system have been targeted at reducing the risk associated with the helper virus. First, replication-competent HSV-1, initially used as helper virus, was replaced by a temperature-sensitive (ts) mutant of HSV-1 (HSV-1 tsK; Preston, C., *J. Virol.* 29:257–284 (1979)). Replication-defective mutants of HSV-1 were then used as helper viruses (Geller, A. I. and Breakefield, X. O., *Science* 241:1667–1669 (1988); Geller, A. I. et al., *Proc. Natl. Acad Sci. USA* 87:8950–8954 (1990); Lim, F., et al., *BioTechniques* 20:458–469 (1996)). These mutants carry mutations in genes that are essential for virus replication, but they can support amplicon packaging in cells that complement the missing functions. However, many problems associated with the presence of helper virus in amplicon stocks still remained.

Many of these problems have been overcome by the more recent development of a packaging system for herpes virus vectors that was free of helper virus (Fraefel, C., et al., *J. Virol.* 70:7190–7197 (1996); International Patent Publication WO 97/05263, published Feb. 13, 1997)). This system utilizes transient co-transfection of amplicon DNA with a set of five cosmids that overlap and represent the entire HSV-1 genome, but which are mutated to delete the DNA cleavage/packaging (pac) signals. Cunningham, C. and Davison, A. J., *Virology* 197:116–124 (1993), had demonstrated previously that after transfection into cells, an overlapping HSV-1 cosmid set can produce infectious virus progeny. By deleting the pac signals and making a pac-minus helper virus genome, HSV-1 genomes that are potentially reconstituted from the cosmids via homologous recombination, are not packageable, but can still provide all the helper functions required for the replication and packaging of the co-transfected amplicon DNA. The resulting vector stocks are, therefore, virtually free of detectable helper virus and have titers of $10^6$–$10^7$ transducing units (tu)/ml of culture medium.

Even more recently, helper virus-free packaging has also been achieved using an oversized pac minus HSV genome, defective in an essential gene encoding ICP27, cloned into a BAC plasmid (Saeki, Y., et al., *Hum Gene Ther* 9:2787–2794 (1998).

If, however, helper viruses are used during propagation of the amplicon, essential genes can be deleted from the helper virus to make it replication incompetent, or carried by the amplicon to make the virus and amplicon interdependent on each other for continued replication and spread (Pechan, P., et al., *Journal of Gene Medicine* 1:176–185 (1999); Chung, R. Y., et al., *J. Virol.* 73:7556–7564 (1999)). Any one of numerous native or modified HSV-1 viruses with various preferred characteristics and therapeutic applications can be used as a helper virus.

For HSV-1 based gene therapy vectors, the potential exists for increasing selectivity for target cells, such as tumor cells, by excising the binding domain in the major cellular attachment protein of the HSV-1 virion, gC. HSV-1 binds to its glucosaminoglycan (GAG) cell surface receptors, principally heparan sulfate (HS), primarily through the HSV-1 viral envelope glycoprotein C (gC), but also gB (WuDunn, D. and Spear, P. G., *J. Virol.* 63:52–58 (1989); Herold, B. C., et al.,*J. Virol.* 65:1090–1098 (1991)). Deletions in the HS binding domain (HSBD) (aa 33–123) allow for protein expression and incorporation into the virion, but significantly decrease non-selective heparan sulfate based cell binding by 34% (Tal-Singer, R., et al., *J. Virol.* 69:4471–4483 (1995)). Soluble heparin completely eliminates attachment and infection by competing with cell surface HS for binding. gB, gD, gH and gL are required for a subsequent membrane fusion and capsid entry step. An erythropoietin epitopic domain has been inserted into the gC HSBD resulting in targeted binding to, but not infection of, erythropoietin receptor bearing cells (Laquerre, S., et al., *J. Virol.* 72:9683–9697 (1998)). As such, a functional targeted HSV-1 vector has not been described.

Despite the development of numerous viral-based vector systems, there exists a need in the art to develop viral-based vectors that can be manipulated to selectively infect only one or few particular types of cell. The availability of a selective and efficient gene delivery system is essential to the success and efficacy of gene-based therapy. The present invention satisfies this need and provides related advantages as well.

SUMMARY OF THE INVENTION

Accordingly, the present invention overcomes the disadvantages of the prior art by providing a herpes simplex viral vector that is cell-type selective and infective.

The present invention provides a herpes simplex virus (HSV) virion comprising HSV amplicon vectors or a mixture of HSV amplicon vectors and recombinant HSV vectors, which are modified to target and infect a selected cell type. The HSV virion contains a restriction site that allows site-specific insertion of a heterologous nucleotide sequence, such that the virion is capable of selectively targeting a particular cell-type. The HSV virions can be derived from HSV-1 or HSV-2, although HSV-1 is particularly preferred.

The invention also provides HSV helper viruses and HSV amplicon vectors, which are cell-type selective.

In a particular embodiment, the invention provides an HSV-1 nucleic acid sequence containing a unique restriction endonuclease site in the heparan sulfate (HS) binding domain of the gC virion cell attachment protein. As disclosed herein, the restriction endonuclease site can be substituted with any other sequence that allows site specific insertion of a heterologous nucleotide sequence, for example, a loxP-Cre recognition and integration site. As a result of this engineering, HSV-1 gC has been modified to selectively target the HSV-1 vectors to particular types of cells.

The invention also provides an HSV-1 amplicon vector targeting system. Such a system can comprise an HSV-1 vector plasmid, an HSV-1 helper virus, or an HSV-1 amplicon vector. The HSV-1 vector plasmid comprises an HSV-1 nucleic acid sequence and a heterologous nucleotide sequence inserted therein. The heterologous nucleotide sequence can be any nucleotide sequence, as desired, particularly a nucleotide sequence encoding a binding domain, which can interact specifically with a ligand expressed by a target cell. Of course, the nucleotide sequence also can encode a ligand, which can be a peptide ligand that specifically binds to a receptor expressed by the target cell.

The invention also provides an efficient method of making or modifying a cell-type selective HSV amplicon vector using a technique known as selective restriction.

The invention also provides a method of introducing a heterologous DNA sequence into a target cell, comprising contacting the target cell with an HSV-1 virion comprising an HSV-1 amplicon vector and/or recombinant virus vector expressing a binding domain, which selectively binds to a molecule expressed by the target cell.

The invention also provides a method of treating a patient with a pathologic condition by using an amplicon vector of the invention to selectively target cells in the patient that are involved in the pathology.

The invention also provides a method of blocking non-specific or non-targeted binding and infection by the HSV-1 virions of the invention through the use of heparin (Trybala, E., et al., *J. Gen. Virol.* 75:743–752 (1994)).

In one exemplary embodiment, the invention provides a method of treating a cancer patient, wherein the cancer cells in the patient express a mutant EGF receptor, comprising: administering to the cancer patient an HSV-1 virion that expresses a cell attachment protein comprising a domain specific for the mutant EGF receptor, wherein the virion intrinsically kills or further contains a DNA sequence, the expression of which kills, reduces or inhibits the growth of, the cancer cell.

In another exemplary embodiment, the invention provides a method of treating a cancer patient, wherein the cancer cells in the patient express an interleukin-4 (IL-4) receptor, comprising: administering to the cancer patient an HSV-1 virion that expresses a cell attachment protein comprising a domain specific for the IL-4 receptor, wherein the virion intrinsically kills or further contains a DNA sequence, the expression of which kills, or reduces or inhibits the growth of, the cancer cell.

It is to be understood that both the foregoing general description and the following detailed description are exemplary and explanatory and are intended to provide further explanation of the invention as claimed.

BRIEF DESCRIPTION OF THE FIGURES

FIG. 1 shows a representation of the pCONGA amplicon. Restriction sites are indicated. "gC" indicates a sequence encoding the major HSV-1 cell attachment protein, glycoprotein C, which contains a heparan sulfate (HS) binding domain. "GFP" indicates a sequence encoding green fluorescent protein. "LacZ" indicates a sequence encoding β-galactosidase, however, the gene has been inactivated. "Neo" indicates a sequence encoding aminoglycoside phosphotransferase (conferring aminoglycoside resistance; in this case, neomycin, resistance).

FIG. 2 shows a representation of pCONGAH, which is derived from the pCONGA amplicon and contains a sequence encoding a polyhistidine tag sequence ("His tag").

FIG. 3 shows a representation of the pCONGA4 amplicon, which is derived from the pCONGA amplicon and contains a sequence encoding an IL-4 receptor binding domain of IL-4 ("IL-4").

FIG. 4 is a representation of a portion of the HSV-1 gC cell attachment protein. Restriction endonuclease recognition sites (ApaI and EcoNI) are shown, as is the heparan sulfate binding domain (HSBD). SP=signal peptide; TM=transmembrane domain; the numbers in the Figure indicate amino acid residues. The cross-hatched box indicates the amino acid sequence of the HSBD reported by Tal-Singer, et al., *J. Virol.* 69:4471–4483 (1995); the open box indicates the amino acid sequence of the HSBD reported by Trybala, E., et al., *J. Gen. Virol.* 75:743–752 (1994).

FIG. 8 depicts GFP fluorescence (FIG. 8A) and lacZ stained (FIG. 8B) micrographs of amplicon/virus, produced from pCONGAH and gCΔ2–3 helper virus, titered onto confluent Vero cells.

Figure 9:
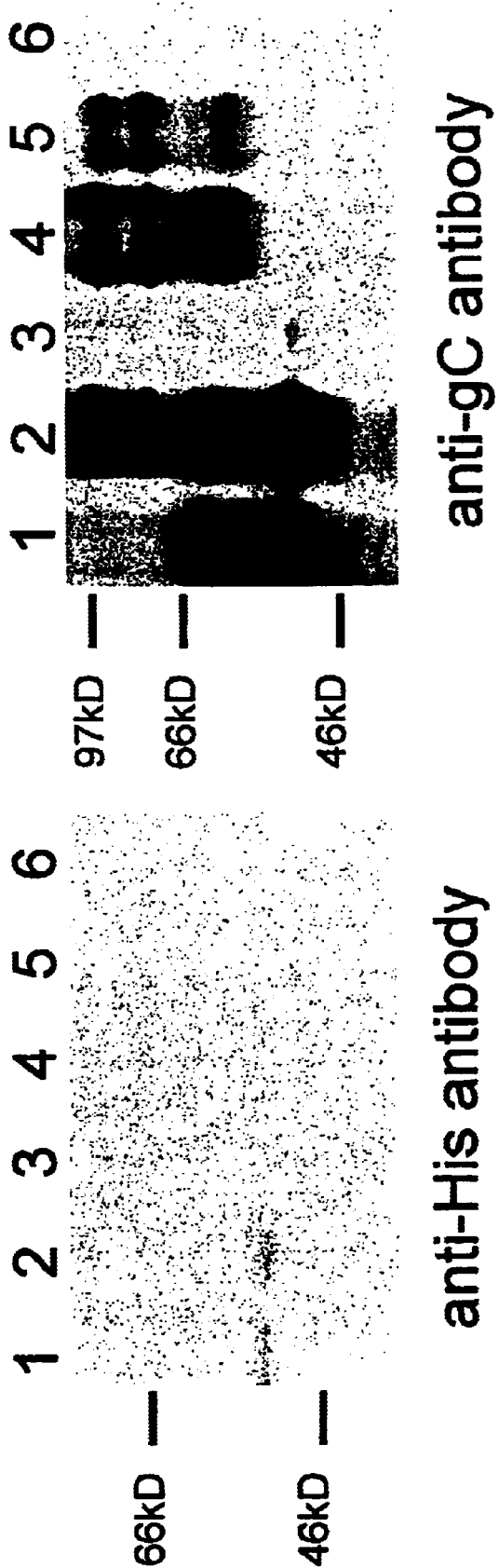

FIG. 9 depicts SDS-PAGE and Western blot analyses of viral protein extracts staining with anti-His tag antibodies and anti-gC antibodies. The figure demonstrates expression of modified gC from pCONGA and pCONGAH transfected cells, with co-localization of modified protein and His tag at appropriate molecular weight (50 kd, with deletion of 142 aa from wild-type gC and insertion of the 15 aa. His tag).

DETAILED DESCRIPTION OF THE PREFERRED EMBODIMENTS

The primary advantage gene therapy offers to the field of oncology is the addition of uniquely engineered mechanisms of eliminating malignant cells. The present invention provides viral vectors, which can be engineered to target and bind to a selected cell or to a plurality of cells expressing a common cell surface molecule.

In one embodiment, the invention provides a herpes simplex virus (HSV) virion comprising HSV amplicon vectors or a mixture of HSV amplicon vectors and recombinant HSV vectors, which are genetically modified to target and infect a selected cell type. The HSV virion contains a restriction site that allows site-specific insertion of a heterologous nucleotide sequence that expresses a targeting domain specific for a molecule expressed by a target cell(s), such that the virion is capable of selectively targeting a particular cell-type. As used herein and throughout, HSV is intended to include any HSV-1 or HSV-2 virus, or derivatives thereof. HSV-1 is particularly preferred.

As used herein, "HSV virion" means an HSV-based particle incorporating and/or packaged from HSV amplicons, HSV virus, or a mixture thereof. Packaging of the amplicon into virions occurs using the functions of an HSV-1 helper virus or a helper-free system (Fraefel, C., et al., *J. Virol.* 70:7190–7197 (1996); International Patent Publication WO 97/05263, published Feb. 13, 1997)).

As used herein, the term "target cell" means a cell to which an amplicon vector of the invention, or the virion containing the amplicon vector, is to be targeted. For example, where it is desired to deliver an HSV amplicon vector to a neoplastic cell, the neoplastic cancer cell is the target cell.

By "neoplastic cells" is meant cells whose normal growth control mechanisms are disrupted (typically by accumulated genetic mutations), thereby providing potential for uncontrolled proliferation. Thus, "neoplastic cells" can include both dividing and non-dividing cells. For purposes of the invention, neoplastic cells include cells of tumors, neoplasms, carcinomas, sarcomas, leukemias, lymphomas, and the like. Central nervous system tumors, especially brain tumors, are particularly preferred. These include glioblastomas, astrocytomas, oligodendrogliomas, meningiomas, neurofibromas, ependymomas, Schwannomas, neurofibrosarcomas, etc. The invention can be utilized to target for oncolysis both benign and malignant neoplastic cells in the periphery and the central nervous system. As used herein, the term periphery is intended to mean all other parts of the body outside of the central nervous system. Breast tumors are particularly preferred peripheral tumors.

The ability of an amplicon vector to selectively target a cell(s) is due to the expression of a targeting domain on the HSV virion. As used herein, the term "targeting domain" means an amino acid sequence that specifically associates with a particular molecule. In general, a targeting domain is a ligand, or a binding domain of a receptor, where the target cell expresses the cognate receptor, or ligand, respectively. However, a targeting domain can also be an epitope for an antibody or, alternatively, an antibody binding domain that is specific for an epitope, which can be expressed by the target cell. As disclosed herein, a targeting epitope can also be a sequence such as a polyhistidine sequence, which can be used to facilitate purification or detection of an amplicon vector.

Exemplary "targeting domains" that may be used to target neoplastic cells include those binding to interleukin-4 receptors (IL-4R), the mutant EGF receptor (EGFRvIII), heregulin, and the prostate-specific membrane antigen (PSMA). Some receptors, such as IL-4R, have natural ligands which contain small, localized domains that specifically bind to the receptor. For receptors without specific natural ligands, phage display technology allows for selection of novel small peptide ligand epitopes.

For oncologic applications, other exemplary targeting domains can be found in Table 1 of Clary, B. M., et al., *Cancer Gene Therapy* 7:565–574 (1998); Table I of Spear, M. A., *Anticancer Research* 18:3223–3232(1998); Table 2 of Walther, W. and Stein, U., *J. Mol. Med.* 74:379–392 (1996); and Dachs, G. U., et al., *Oncol. Res.* 9:313–325 (1997)).

Specific targeting epitopes for tumor targeting include: those that have been derived from genes that encode tyrosinase (allowing for targeting to melanoma) (Vile, R. G. and Hart, I. R., *Cancer Res.* 53:962–967 (1993); Vile, R. G. and Hart, I. R., *Ann. Oncol* 5 (Suppl. 4):S59–S65 (1994); Hart, I. R., et al., *Curr. Opin. Oncol.* 6:221–225 (1994)); c-erbB-2 oncogene (targeting to breast, pancreatic, gastric, and ovarian cancers) (Hollywood, D., and Hurst, H., *EMBO J* 12:2369–2375 (1993)); carcinoembryonic antigen (CEA) (targeting to lung and gastrointestinal malignancies, including colon, pancreatic, and gastric cancer) (Thompson, J. A., et al.,*J. Clin. Lab. Anal.* 5:344–366 (1991); Osaki, T., et al., *Cancer Res.* 54:5258–5261 (1994)); DF3/MUC1 (targeting to breast cancer) (Abe, M. and Kufe, D., *Proc. Natl. Acad Sci. USA* 90:282–286 (1993); Manome, Y., et al., *Gene Ther.* 2:685, A051 (1995); Chen, L., et al., *J. Clin. Invest.* 96:2775–2782 (1995)); prostate specific antigen(PSA) (targeting to prostate cancer) (Lundwall, A., *Biochem. Biophys. Res. Commun.* 161: 1151–1156 (1989)); and alpha-fetoprotein (AFP)(targeting to hepatocellular carcinoma) (Arbuthnot, P., et al.,*Hepatology* 22:1788–1796 (1995); Ido, A., et al., *Cancer Res.* 55:31053109 (1995)). The use of synthetic gene regulation systems, which allow for transcriptional control and other forms of regulated expression may also be used (Miller, N. and Whelan, J., *Hum. Gene*

Ther. 8:803–815 (1997); Vile, R. G., Semin. Cancer Biol. 5:429–436 (1994); Hwang, J. J., et al., J. Virol. 70:8138–8141 (1996); Massie, B., et al., J. Virol. 72:2289–2296 (1998)).

Tumor cells are also known to overexpress particular oncogenes, so that cells with upregulated gene expression can be targeted using promoter elements of such genes. B-myb, C-myb, c-myc, c-kit, and the c-erbB2 oncogene are some representative examples of these types.

Numerous other targeting epitopes that target cell types other than neoplastic cells may be used in the vector of the present invention, and will be known to those skilled in the art. Some examples include receptors for neurotransmitters on specific neurons (i.e., dopamine D2R), channels, transporters, and receptors for growth factors (i.e., VEGF). See, for example, (Missale, C., et al., Physiol. Rev. 78: 189–223 (1998); Rour, S., et al., Microbiol. Rev. 59:63–93 (1995); Sheng. M and Pak D T, Ann. Rev. Physiol. 62:755–778 (2000)).

Most if not all of the gene sequences of the above mentioned tumor-specific targeting domains are available from the GenBank Sequence Database.

A specific, but non-limiting, example of an HSV-1 amplicon plasmid constructed by the present inventors is "pCONGA" (FIG. 1). pCONGA has been engineered to contain unique restriction sites in the nucleic acid sequence encoding the major cell attachment protein of the HSV-1 virion, gC. As a result, the nucleotide sequence encoding the heparan sulfate (HS) binding domain of gC can be rapidly excised and replaced by a nucleotide sequence encoding a selected targeting domain, which binds to a molecule expressed by a target cell.

More specifically, pCONGA carries a gC gene that has been modified to contain unique restriction endonuclease sites that flank the HS binding domain (residues 33–176), thereby allowing ready substitution of the HS domain with a nucleic acid sequence encoding a selected targeting domain. Such a substitution allows HSV-1 amplicon and virus infection/transduction to be targeted to specific tissues, cells, or tumors, respectively. The modified gC is expressed on amplicon and helper virus virions produced from cells transfected with pCONGA and helper virus genome.

Another non-limiting example of an HSV-1 amplicon plasmid constructed by the present inventors is "pCONGAH" (FIG. 2). This HSV-1 amplicon plasmid carries the gC gene, along with a His tag (FIG. 6), which provides a means for selection. pCONGAH was produced by recombining a nucleic acid sequence encoding a His tag into the pCONGA HS binding domain. Western blot analysis demonstrated that infection of pCONGAH transfected Vero cells with HSV-1 helper virus (hrR3) resulted in the expression of His-modified gC. More specifically, Western blot analysis revealed colocalization of anti-gC antibodies and anti-His tag antibodies to a protein having the appropriate 50 kilo-Dalton molecular mass.

Another non-limiting example of an HSV-1 amplicon plasmid constructed by the present inventors is "pCONGA4" (FIG. 3) This amplicon plasmid was constructed by inserting the IL-4 receptor binding epitope into gC (Puri, R. K., et al., *Int. Jnl Cancer* 58:574–581 (1994)). This amplicon plasmid is useful for targeting neoplastic cells that express IL-4.

*E. coli* strains containing plasmids pCONGA, pCONGAH and pCONGA4 were deposited at the American Type Culture Collection (ATCC), 10801 University Blvd., Manassas, Va. 20110–2209, USA, on May 16, 2001, Apr. 23, 2001 and May 23, 2001, respectively. The ATCC has assigned the *E. coli* clones harboring these plasmids deposit numbers PTA3380 (pCONGA), PTA-3323 (pCONGAH), and PTA-3396 (pCONGA4).

The amplicon system exemplified herein provides at least one, but preferably two, unique restriction site(s), which allows specific recombinant insertion and selection; an amplicon plasmid, which is conveniently manipulated; a neomycin resistance marker, which allows for antibiotic selection; a GFP marker gene, which allows for quantification and tracking; a His tag, which allows selection; or an IL-4 receptor binding epitope, which allows targeting of tumor cells that express an IL-4 receptor.

Variations of the exemplified embodiments will be known to those skilled in the art. For example, the insertion site can be based on the loxP-Cre system for site specific insertion of a sequence; the neomycin resistance gene can be substituted with any convenient or desirable selection system; the His tag can be substituted with any epitope for which a binding reagent, for example, an antibody is available; and the targeting domain can be any targeting domain specific for a selected target cell.

CONGA derived plasmids are transfected into Vero cells, which are subsequently infected with helper virus. This produces viruses and amplicons, (modified "virions") carrying the modified gC gene. Amplicons also can carry nucleic acid sequences encoding a marker such as GFP or neomycin. They may also carry a therapeutic or diagnostic gene.

Any virus can be used, particularly a virus deleted for gC, gB, and/or gD, or viruses otherwise modified to assist in decreasing non-specific infection or specific infection. For example, other proteins in the HSV virion can be modified including other envelope glycoproteins, tegument proteins, or capsid proteins.

The amplicon vector alone can also be produced using helper virus free amplicon systems, such as those described in Fraefel, C., et al., *J. Virol*. 70:71907197 (1996); International Patent Publication WO 97/05263, published Feb. 13, 1997) or Saeki, Y., et al., *Hum Gene Ther* 9:2787–2794 (1998).

Virus carrying a therapeutic gene for cancer or other diseases, including diseases having a genetic basis, can be used, and the gene contained in the virus can correct a genetic defect, can kill a cell, or can have any other action, as desired. Viruses or other virus-derived sequences having intrinsic cytotoxic, therapeutic, or diagnostic effects may also be used. Modified gC targets infection to the target cell, thus producing selective delivery of a therapeutic or diagnostic gene or virus function to the cell. The histidine tag, or other suitable labeling ligand known to those skilled in the art, can also be used to trace gC and select and purify virus and amplicon.

Heparin may also be used to further decrease non-specific heparan sulfate binding activity in the HSV virion of the invention. See, Trybala, E., et al., *J. Gen. Virol*. 75:743–752 (1994).

Incubation of the product vectors with a selective His binding to antibodies or a nickle nitriloacetic acid (Ni-NTA) matrix, followed by washing, elution and comparison of eluant titers, may demonstrate the functional presentation of His-modified gC on virions. Thus, using a Ni-NTA matrix or anti-His antibodies provides a convenient means to purify His-tagged amplicons and virions. The substitution of a tumor targeting epitope for the HS binding domain can ablate residual heparan sulfate binding activity within the HSV-1 gC glycoprotein and substitute therefore tumor cell binding specificity.

The invention also provides HSV-1 helper viruses and amplicon vectors, which are cell-type selective.

In a particular embodiment, the invention provides an HSV-1 nucleic acid sequence containing a unique restriction endonuclease site in the heparan sulfate (HS) binding domain of the gC virion cell attachment protein. As disclosed herein, the restriction endonuclease site can be substituted with any other sequence that allows site specific insertion of a heterologous nucleotide sequence, for example, a loxP-Cre recognition and integration site. As a result of this engineering, HSV-1 gC has been modified to selectively target the HSV-1 vectors to particular target cells.

The invention also provides an HSV-1 amplicon vector targeting system. Such a system can comprise an HSV-1 vector plasmid, an HSV-1 helper virus, and/or an HSV-1 amplicon vector. The HSV-1 vector plasmid comprises an HSV-1 nucleic acid sequence and a heterologous nucleotide sequence inserted therein. The heterologous nucleotide sequence can be any nucleotide sequence, as desired, particularly a nucleotide sequence encoding a binding domain, which can interact specifically with a ligand expressed by a target cell. Of course, the nucleotide sequence also can encode a ligand, which can be a peptide ligand that specifically binds to a receptor expressed by the target cell.

The invention also provides an efficient method of making or modifying a cell-type selective HSV-1 amplicon vector using a technique known as selective restriction.

The invention also provides a method of introducing a heterologous DNA sequence into a target cell, comprising contacting the cell with an HSV-1 amplicon vector expressing a binding domain, which selectively binds to a molecule expressed by the target cell.

The invention also provides a method of treating a patient with a pathologic condition by using the modified HSV virion of the invention to selectively target cells in the patient that are involved in the pathology.

In one exemplary embodiment, the invention provides a method of treating a cancer patient, wherein the cancer cells in the patient express a mutant EGF receptor, by administering to the cancer patient an HSV virion that expresses a cell attachment protein comprising a domain specific for the mutant EGF receptor, wherein the virion may further contain a DNA sequence (also called "transgene"), the expression of which kills, reduces, or inhibits the growth of, the cancer cell.

In another exemplary embodiment, the invention provides a method of treating a cancer patient, wherein the cancer cells in the patient express an interleukin-4 (IL-4) receptor, by administering to the cancer patient an HSV virion that expresses a cell attachment protein comprising a domain specific for the IL-4 receptor, wherein the virion may further contain a DNA sequence, the expression of which kills, reduces, or inhibits the growth of, the cancer cell.

In addition to having a particular targeting domain inserted in the HSV virion (the amplicon vector or the amplicon/recombinant virus mixture), the HSV helper virus can also carry the heterologous transgene.

In another embodiment, the helper virus has intrinsic cytotoxic, therapeutic, or diagnostic properties.

The transgene can be a suicide gene, that is, a gene that encodes a gene product capable of activating a chemotherapeutic agent to its cytotoxic form, such as HSV-TK, CD, or cytochrome P450. By "gene product capable of converting a chemotherapeutic agent to its cytotoxic form" is meant a gene product that acts upon the chemotherapeutic agent to render it more cytotoxic than it was before the gene product acted upon it. Other proteins or factors may be required, in addition to this gene product, in order to convert the chemotherapeutic agent to its most cytotoxic form.

By "transgene encoding a gene product capable of converting a chemotherapeutic agent to its cytotoxic form" is meant a nucleic acid that upon expression provides this gene product.

"Cytotoxic" is used herein to mean causing or leading to cell death.

"Gene product" broadly refers to proteins encoded by the particular gene.

"Chemotherapeutic agent" refers to an agent that can be used in the treatment of neoplasms, and that is capable of being activated from a prodrug to a cytotoxic form.

Other chemotherapeutic agent/transgene combinations for use in the present invention will be known to those skilled in the art.

In addition to, or in lieu of a "suicide gene," the transgene can also encode a cytokine to stimulate or enhance a tumor-directed immune response. See, Blankenstein, T., et al., *J. Exp. Med.* 173:1047–1052 (1991); Colombo, M. P., et al., *Cancer Metastasis Rev.* 16:421–432 (1997); Colombo, M. P., et al., *Immunol. Today* 15:48–51 (1994)). Representative examples include tumor necrosis factor alpha (TNF-$\alpha$), interferon-$\gamma$, interleukins (IL-2, IL-4), or granulocyte-macrophage colony stimulating factor (GM-CSF)).

The transgene could also encode a tumor suppressor gene, or any other tumoricidal gene known to those skilled in the art, such as diptheria toxin (Coll-Fresno, P. M., et al., *Oncogene* 14:243–247 (1997)), pseudomonas toxin, anti-angiogenesis genes, tumor vaccination genes, radiosensitivity genes, antisense RNA, or ribozymes (Zaia, J. A., et al., *Ann. N. Y Acad. Sci.* 660:95–106 (1992)).

Thus, in this embodiment of the invention, the altered HSV virion of the invention, described herein, further comprises a transgene encoding a gene product capable of converting a chemotherapeutic agent to its cytotoxic form or any other tumoricidal transgene, as mentioned above. The transgene can be inserted in the HSV amplicon in any location where it will be expressed. If, however, the transgene is inserted in the helper virus genome, the following locations would be preferred: RR, gamma 34.5, gB, or gC.

Exemplary candidates for treatment according to the presently claimed methods include, but are not limited to: (i) non-human animals suffering from neoplasms characterized by a tumor-specific or cell-type specific surface protein; (ii) humans suffering from neoplasms characterized by a tumor-specific or cell-type specific surface protein; or (iii) humans or non-human animals in need of eradication of a particular cell population.

By "neoplastic cells" is intended cells whose normal growth control mechanisms are disrupted (typically by accumulated genetic mutations), thereby providing the potential for uncontrolled proliferation. The term is intended to include both benign and malignant neoplastic cells in both the central nervous system and the periphery. As used herein, the term "periphery" is intended to mean all other parts of the body outside of the central nervous system (brain or spinal cord).

For purposes of the invention, neoplastic cells include cells of tumors, neoplasms, carcinomas, sarcomas, papillomas, leukemias, lymphomas, and the like. Of particular interest are solid tumors that may arise in any organ or tissue of the mammalian body.

Malignant brain tumors, include astrocytoma, oligodendroglioma, meningioma, neurofibroma, glioblastoma, ependymoma, Schwannoma, neurofibrosarcoma, and medulloblastoma.

Preferentially, the treatment will be initiated by direct intraneoplastic inoculation or systemic intravascular administration (taking advantage of the targeting properties of the vector). For tumors in the brain, MRI, CT, or other imaging guided stereotactic techniques may be used to direct viral inoculation, or virus will be inoculated at the time of craniotomy. For patients attempting to eradicate a particular target cell population, the vector would be inoculated into the tissue of interest.

Generally, methods are known in the art for viral infection of the cells of interest. For example, the viral mutant can be injected into the host at or near the site of neoplastic growth, or administered by intravascular inoculation. Typically, the viral mutant would be prepared as an injectable, either as a liquid solution or a suspension; a solid form suitable for solution in, or suspension in, liquid prior to injection may also be prepared. The preparation also may be emulsified. The active ingredient is preferably mixed with an excipient which is pharmaceutically-acceptable and compatible with the active ingredient. Suitable excipients are, for example, water, saline, dextrose, glycerol, or the like and combinations thereof. In addition, if desired, the preparation may contain minor amounts of auxiliary substances such as wetting or emulsifying agents, pH-buffering agents, adjuvants or immunopotentiators which enhance the effectiveness of the viral mutant (See, *Remington's Pharmaceutical Sciences*, Gennaro, A. R. et al., eds., Mack Publishing Co., pub., 18th ed., 1990). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. Determining the pH and exact concentration of the various components of the pharmaceutical composition is routine and within the knowledge of one of ordinary skill in the art (See *Goodman and Gilman's The Pharmacological Basis for Therapeutics*, Gilman, A. G. et al., eds., Pergamon Press, pub., 8th ed., 1990).

Additional formulations which are suitable include oral formulations. Oral formulations include such typical excipients as, for example, pharmaceutical grades of mannitol, lactose, starch, magnesium stearate, sodium saccharine, cellulose, magnesium carbonate and the like. Oral compositions may take the form of tablets, pills, capsules, sustained release formulations or powders and contain 10%–95% of active ingredient, preferably 25–70%.

The dosage of the viral mutant to be administered, in terms of number of treatments and amount, depends on the subject to be treated, the capacity of the subject's immune system to synthesize antibodies, and the degree of protection desired. Precise amounts of active ingredient required to be administered depend on the judgment of the practitioner and are peculiar to each individual. For the most part, the virus is provided in a therapeutically effective amount to infect and kill target cells.

The present invention is further illustrated by the following examples. These examples are provided to aid in the understanding of the invention and are not construed as a limitation thereof.

EXAMPLE 1

Construction and Evaluation of pCONGA and pCONGAH

HSV-1 based vectors can exist in the form of either a modified HSV-1 genome or an amplicon. Amplicon plasmids are standard *E. coli*-based plasmids containing the HSV-1 origin of replication "oriS" and packaging "a" (or pac) sequences along with transgene(s). If transfected into cells infected with a helper virus, these sequences allow replication and packaging of the plasmid into infectious HSV-1 virions to form amplicon vectors. Sequences for HSV-1 proteins can be carried in the amplicon plasmid allowing in trans expression and incorporation into both progeny virus and amplicon particles.

Recombinant addition of a His tag into a protein provides a means for selectively isolating or purifying the His-tagged protein (Sulkowski, E., *Trends in Biotechnology* 3: 1–7 (1985)). By running a sample through a nickel-nitrilotriacetic acid affinity matrix (Ni-NTA; QIAexpress™), the His-tagged polypeptide can be bound, then eluted.

Figure 1:
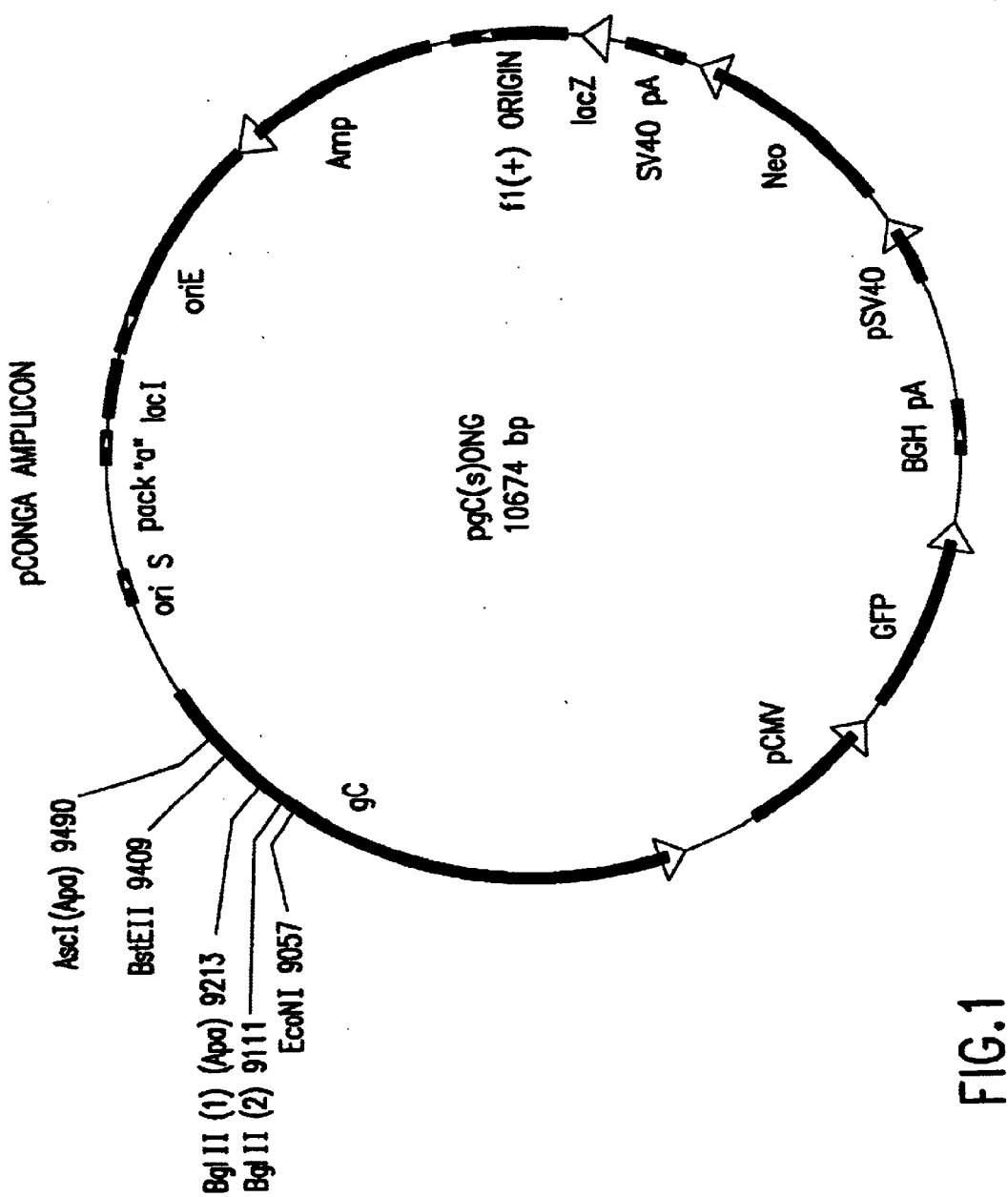
Figure 2:
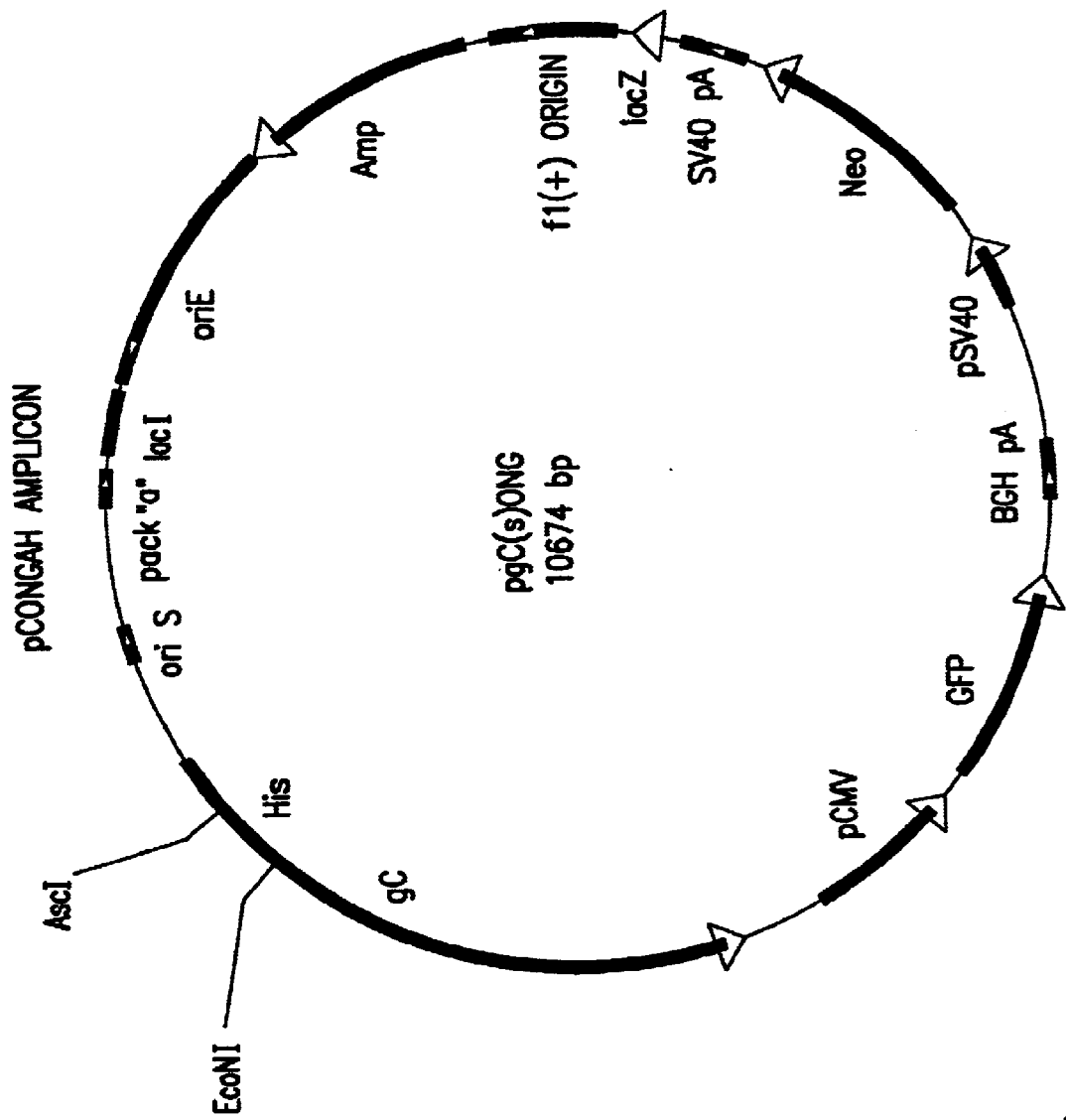

A His tag was inserted into the HSV-1 gC HS binding domain in a gC-containing HSV-1 amplicon plasmid (pCONGA; FIG. 1) to create pCONGAH (FIG. 2). Titers of progeny virus were increased when selected on and eluted from a Ni-NTA matrix. Production of the modified gC protein was characterized by Western blot analysis. The ability to express functional, targeted, modified gC has been demonstrated. An additional advantage is that sample titers were increased.

Methods

Construction of pCONGA Amplicon Plasmid

The selective restriction method of Spear (Spear, M., *BioTechniques* 28:660–668 (2000)) was used to place the HSV-1 gC gene (provided by Curtis R. Brandt, Northwestern University) into the PstI and HindIII sites of an amplicon plasmid previously constructed with the HSV-1 oriS and pac sequences (provided by Dora Ho of Stanford University) in pBluescript (Invitrogen). Subsequently, a cassette carrying the (enhanced green fluorescent protein) EGFP and Neo$^r$ genes (InVitrogen) was inserted into the XhoI site. Site-directed mutagenesis was then used to add a unique AscI restriction site to complete construction of the pCONGA amplicon plasmid targeting system, with AscI and EcoNI unique restriction sites flanking (amino acid residues 33–176) the HS binding domain (HSBD) of gC (aa 33–155) for exchange of targeting epitopes (FIG. 1).

Construction of pCONGAH Amplicon Plasmid

Using 42 bp synthetic AscI and EcoNI cohesive ended oligonucleotides, a His tag sequence was then recombined into the AscI and EcoNI sites of pCONGA, replacing the HSBD to create pCONGAH (FIG. 2). pCONGAH carries a modified HSV-1 gC attachment glycoprotein gene to allow co-expression of modified gC in product amplicon and virus for vector targeting, a marker His tag in gC for system characterization, a GFP marker gene, and a neomycin resistance gene to allow for long term, large quantity generation of transfected producer cells and vector. The HSV-1 gC gene carried by CONGAH has been engineered to have unique restriction sites (AscI and EcoNI) flanking the HSBD, and a unique restriction site (HpaI) within the His tag insert. The His tag sequence was designed to contain a unique Hpa I site to allow rapid screening of subcloning output through addition of a new unique site, and the insertion of various targeting epitopes using the selective restriction method (Spear, M., BioTechniques 28:660–668 (2000), in which case restriction digested plasmid and insert are directly combined and ligated followed by digestion with the selective restirction endonuclease to prevent production of back recombinants The resulting plasmid was confirmed with fluorescent ABI big dye-tag sequencing.

Evaluation of pCONGA and pCONGAH

Modified amplicon and viral vectors were produced using hrR3 HSV-1 virus as the helper virus (ribonucleotide reductase deleted, lacZ marker transgene) (Goldstein D J and Weller S K, Virology 166:41–51 (1988)). The HSV-1 vector, hrR3, provides selective cytotoxicity to tumor cells through both intrinsic viral toxicity and the thymidine kinase (TK) gene it carries (TK activates the prodrug ganciclovir). HSV-1 vectors bearing other transgenes can easily be substituted.

Modified gC carried by amplicon plasmid was expressed on both amplicon and virus produced in co-infected cells. Analysis of viral protein extract using SDS-PAGE and Western blot with anti-His tag MAb and anti-gC MAb confirmed colocalization of protein and tag. Stable transfectant Vero cells were produced as viral producer cells in order to generate large quantities of vector.

In other experiments, a gC deleted virus (gCA2–3) (Herold, B. C., et al., J. Gen. Virol. 75:1211–1222 (1994)), at a MOI of 0.3, was used as a helper virus. As CONGA and CONGAH amplicons carry a green fluorescent protein (GFP) transgene (see, FIGS. 1 and 2), and gCΔ2–3 carries the lacZ transgene, the transfection-infection product amplicon and helper virus vectors were titered on Vero cells and transduction units quantified.

Using gCΔ2–3, four generations of vector were produced over two months of continuous culture growth under selection. Cultures were also cryopreserved and subsequently used for vector production. Titers of amplicon, quantified using the GFP marker gene, remained at $2\times10^5$/mL; helper virus, quantified using the lacZ marker gene, remained at $2\times10^7$/mL. Nonselected cells produced no detectable amplicon after 2 weeks.

Production of Modified Amplicon and Virus

Vero cells growing in DMEM/10%FBS/1% penicillin-streptomycin ($1\times10^5$) were transfected with pCONGAH or pCONGA using Lipofectamine™ (Life Technologies) per manufacturers protocol. Modified amplicon and virus was produced by infection with gC deleted helper virus (gCΔ2–3) supplied by Curtis R. Brandt, Northwestern University) at multiplicity of infection (MOI)=0.3 in 1 ml OptiMem media (Gibco) in 6 well plates. After 48 hours, amplicon and virus were harvested using 3 freeze-thaw cycles. Debris was removed by centrifugation at 1400×g. Optimized titers were obtained by decreasing incubation media to 500 μl DMEM with 10% FBS and 1% Penicillin-Streptomycin, sonicating after freeze-thaw, and titering onto a minimal volume of 100 μl.

Titering of Modified Amplicon and Virus $7.5\times10^4$ Vero cells were plated onto 24-well plates in 0.5 ml. 24 hours later, harvested amplicon/virus was titered onto the confluent cells in 10–100,000-fold dilutions. After 16 hours, the number of cells producing EGFP with fluorescence microscopy (ab-em) were counted in an evaluable dilution. Cells were then fixed with 4% paraformaldehyde, stained with X-gal, and the number of cells producing lacZ with light microscopy were counted in an evaluable dilution after 24 hours.

Western Blot to Demonstrate Production of Modified gC

SDS-PAGE was run with amplicon transfected and/or virus infected cells or purified amplicon/virus lysed in SDS-buffer. The gel was then blotted onto transfer membrane in transfer buffer (25 mM Tris, 192 mM Glycine, 20% MeOH) at 4° C. The membrane was incubated in 100% MeOH for 10 seconds and blocked with 3% casein/TBS solution for 1 hour at room temperature (RT). The membrane was washed twice for 5 minutes in 0.05% Tween-20, TBS solution (TTBS). The membrane was incubated with mouse anti-RGS-His or anti-HSV-1 gC for 90 minutes in probing buffer (20 mM Tris-HCL, 250 mM NaCL, 0.05% Tween 20, 1% casein) at RT, then washed in TTBS. The membrane was then incubated with HRP-coupled anti-mouse Ig antibody for 30 minutes at RT, washed and developed with DBT.

Generation of Amplicon Producer Cell Lines

Two days following transfection of pCONGAH into Vero cells as described above, the media was replaced with DMEM/10%FBS/1% penicillin-streptomycin containing 0.8 mg/ml G418 (Genetacin, Sigma). Subsequently, cells were split 1:5 and 1:2 into media containing 0.8 mg/ml G418 on alternating weeks. Infection with gCΔ2–3, harvesting, and titering was performed as described above every 2 weeks. G418 containing media was changed to standard media 24 hours prior to infection.

Results

Construct of pCONGA and pCONGAH Plasmids

The pCONGA and pCONGAH plasmids were constructed as detailed in Methods, above, to contain the HSV-1 gC attachment protein with the HSBD flanked by two (2) unique restriction sites, the HSV-1 amplicon origin of replication (ori$_s$) and packaging sequence (pac), EGFP, and neomycin resistance (FIG. 2). pCONGAH additionally contains a His tag replacing the HSBD. Recombinations were confirmed by DNA sequencing. Function of amplicon components, EGFP, and neomycin resistance was confirmed by amplicon production, fluorescence microscopy, and G418 selection as described in Methods. Efficient insertion of a targeting epitope using HpaI selective restriction digest was confirmed with the insertion of an IL-4 domain. See, Spear, M., BioTechniques 28:660–668 (2000), and Example 2 below.

Production of Amplicons and Virus

Amplicon and virus mixtures carrying modified gC were produced by transfecting pCONGA and pCONGAH into Vero cells and subsequently infecting with a gC deleted helper virus. As the viral particles carry lacZ and the amplicon particles carry GFP, the product has been titered for transduction of Vero cells using fluorescence microscopy and X-gal staining, and demonstrated to contain titers of $2\times10^5$ amplicons/ml and $1\times10^7$ virus/ml. (FIG. 8).

Western Blot to Demonstrate Production of Modified gC

Analysis of viral protein (FIG. 9) extracts using SDS-PAGE and Western blot with anti-His tag antibodies and anti-gC antibodies confirms production of modified gC from pCONGA and pCONGAH transfected cells with co-localization of modified protein and tag at appropriate molecular weight (50 kd, with deletion of 142 aa from wild-type gC and insertion of the 15 amino acid His tag). Expression is regulated by the native gC promoter which necessitates the presence of transactivating factors supplied by HSV-1 virions, as modified gC is below levels of detection in cells that have been transfected with amplicon, but detectable following infection or transfection of such cells with a helper virus. Expression of unmodified wild type gC is also seen in cells transfected with pCONGA and/or infected with hrR3 which carries wild type gC.

Generation of Amplicon Producer Cell Lines

Continuous application of G418 (0.8 mg/ml) in culture media was used to select for amplicon transfected Vero cells.

The generation of stable long term amplicon producer cells demonstrated that at 2 months after transfection, infection of these cells with helper virus continued to produce titers of $2 \times 10^5$ amplicons/ml and $1 \times 10^7$ virus/ml. Producer cells were also cryopreserved and continued amplicon production was seen when thawed. This is a previously undescribed and potentially useful application for large scale production of amplicon and virus.

Discussion

The results in this Example demonstrate that the described amplicon construct allows for expression of a functional modified HSV-1 gC protein and production of viral and amplicon particles functional for gene transfer. His tag-modified protein was detected by Western blot. This suggests that other targeting epitopes may be similarly functionally expressed. Transduction of cells with GFP carried by the amplicon and lacZ carried by the helper virus was seen, indicating that the virus retained function. MTT assays were also performed on glioblastoma tumor cell lines after infection with modified amplicon/virus (hrR3) and demonstrated retention of oncolytic activity.

This system is particularly useful secondary to the ease of manipulation in a simple E. coli based plasmid. The efficiency of application is further improved by the engineered inclusion of a unique HpaI restriction site to allow for rapid recombination using the selective restriction method for the insertion of other targeting epitopes, which has been accomplished using oligonucleotides coding for the IL-4 receptor binding domain (Spear, M., BioTechniques 28:660–668 (2000)). Possible targeting epitopes are numerous, and for example in oncologic disciplines include IL-4, EGF, heregulin and others. Phage display can also be used to select small peptide epitopes for selectively expressed cell surface receptors for which naturally occurring ligands are not known.

A preference is held for small continuous epitopes to minimize potential interference in folding, presentation, translocation and expression on the virion surface. As each epitope possibly inserted can have an individualized interaction with the surrounding gC sequence, and possibly incur any of the above problems resulting in a non-functional epitope or gC. Testing the insertion of tumor targeting epitopes including the IL-4 receptor binding epitope is in progress. Initial studies with amplicon and viral titers indicate similar results as seen with pCONGAH.

Another previously undescribed advantage of the system is the ability to generate producer cell lines based on selection with G418 given the presence of the Neo resistance gene. Infection with helper virus results in the lysis of amplicon plasmid transfected cells and non-selected cells fail to retain the plasmid during successive replication, thus the size of each batch of amplicon is limited by the amount of reagents utilized in transfection and each new batch requires a new transfection. Using this system with G418 selection and cryopreservation, nearly unlimited quantities can be produced over any time period.

The flexibility of the amplicon system in term of vector production methods is further of extraordinary benefit. The selective oncolytic ribonucleotide reductase deficient HSV-1 vector hrR3 has been used as a helper virus to obtain similar results titers, thus demonstrating the interchangeable applicability of the system to different therapeutic vectors. Previously, the hrR3 vector was utilized with MTT assays to demonstrate oncolytic activity in glioma, pancreatic carcinoma and cervical carcinoma cells (Spear, M. A. et al., Cancer Gene Therapy 7:1051–1059 (2000)). Targets for which non-cytotoxic gene transfer is desired, such as gene replacement in functional cells, helper-free cosmid systems (Fraefel, C., et al., Molecular Medicine New York 3:813–825 (1997)) or replication deficient helper viruses can also be used (Glorioso, J. C. et al., Annu Rev. Microbiol. 49: 675–710(1995); Krisky, D. M. et al., Gene Ther 5:1517–1530 (1998)).

EXAMPLE 2

Production and Evaluation of pCONGA4, an HSV-1 Amplicon Vector Carrying gC Modified With the IL-4 Receptor Binding Domain Replacing the HS Binding Domain of gC A number of protein moieties have been characterized that have demonstrated potential for targeting vectors to a malignant cell via ligand-receptor interactions. For example, interleukin-4 (IL-4) receptors are over-expressed in gliomas, breast cancers, and other tumors, and IL-4 toxin conjugates have been shown to target tumor cells (Puri, R. K., et al., Proceedings of the American Association for Cancer Research Annual Meeting 37: 417 (1996)).

Figure 3:
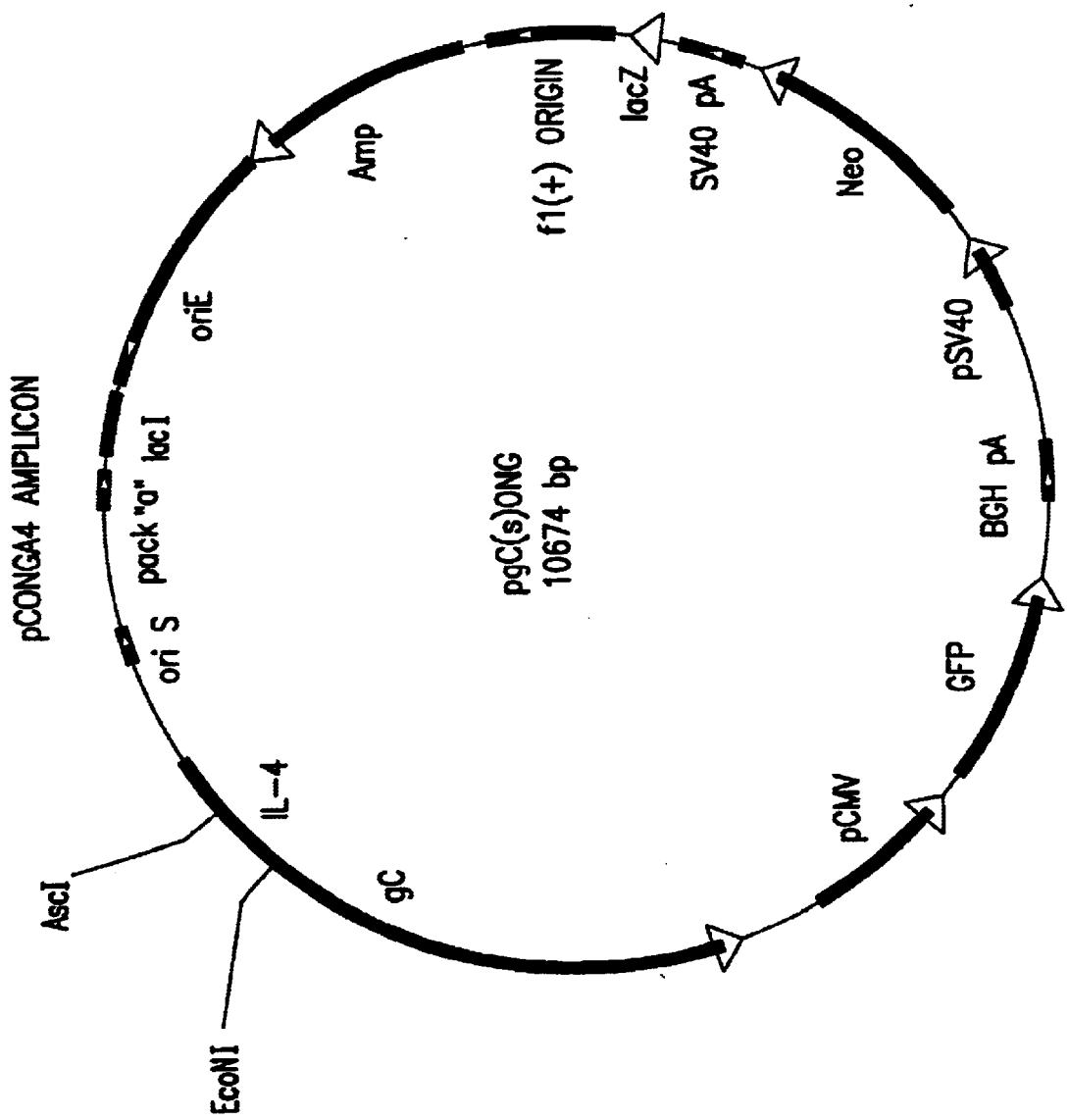
Figure 4:
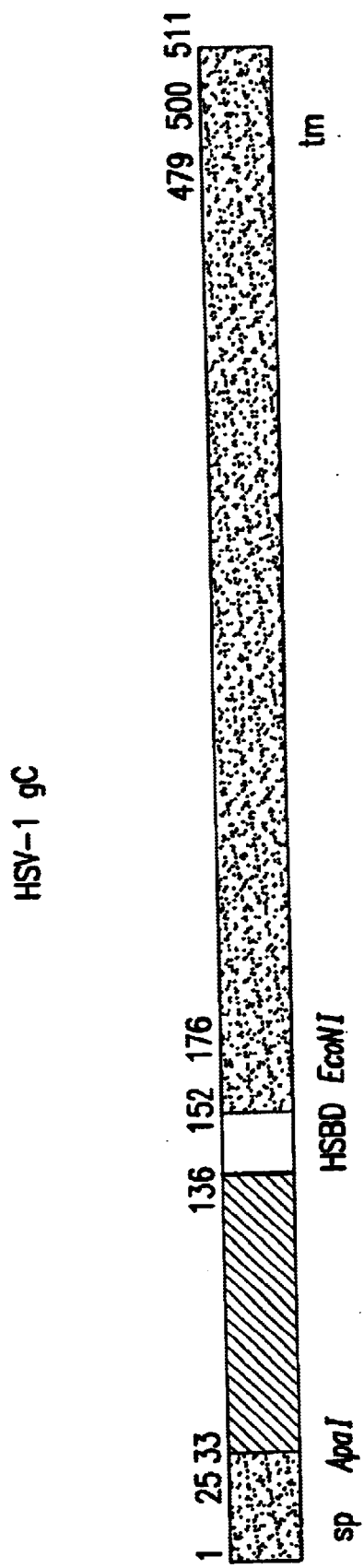
Figure 5:
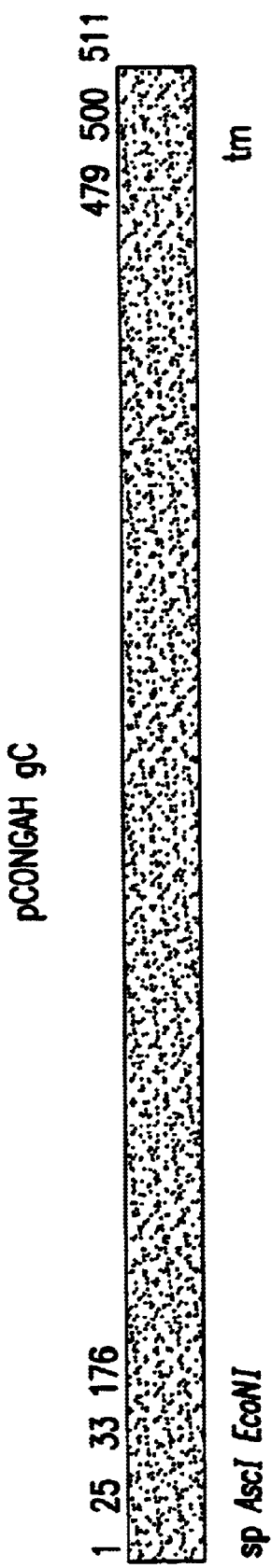
FIG. 5 shows a representation of a portion of the gC polypeptide in pCONGAH.
Figure 6:
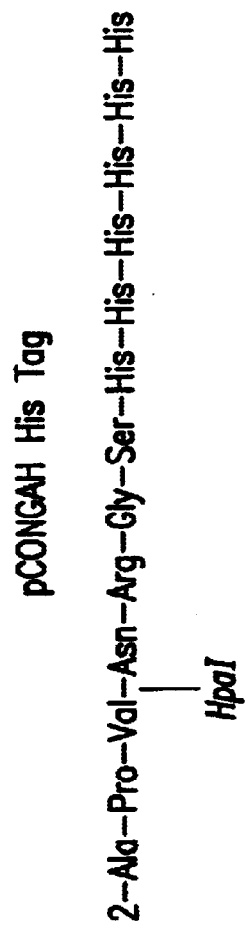
FIG. 6 shows a portion of the amino acid sequence of the sequence shown in FIG. 5 that includes the polyhistidine sequence ("His tag").

As disclosed herein, an IL-4 receptor binding domain of IL-4 was inserted into the gC HS binding domain in pCONGA to create pCONGA4 (FIG. 3). This vector can target virus and amplicon to cells that over-express IL-4 receptors. Transduction efficiencies can be measured by titering on stable transfectant IL-4 receptor over-expressing cells compared to non-expressing cells to test selectivity. The constructs also can be tested on IL-4 receptor over-expressing tumor cell lines, including glioblastoma and breast carcinoma cells. Other tumor selective binding domains can be inserted and tested, as desired. The targeted vectors can be examined, if desired, in animal model systems, for example, rat or murine tumor models.

Methods

The pCONGA4 amplicon plasmid, with IL-4 receptor binding domain of human IL-4 recombined into AscI and EcoNI sites of gC in pCONGA, was prepared using the HpaI selective restriction method (Spear, M., Biotechnology 28:660–668 (2000), which is incorporated by reference in its entirety.

Vero cells were transfected (Lipofectamine™) with amplicon constructs pCONGA4, and infected with a gC deleted helper virus. The virus and amplicon expressing modified gC were harvested by freeze-thaw.

SDS-PAGE viral protein and Western blot with anti-IL-4 MAb and anti-gC Mab were carried out. Modified virus/amplicon and control (unmodified) were incubated on IL-4 receptor stable transfectant cell lines and control cell lines (parental), then washed, and incubated. As the amplicon contains the GFP gene and the virus contains lacZ, titers (transduction efficiency) were determined using fluorescence microscopy and X-gal staining. This can be done on U87 glioma and ZR-75-1 breast tumor lines that endogenously overexpress IL-4.

Human U87 glioma and ZR-75-1 breast tumor cell lines overexpressing IL-4 receptors can be implanted in the flanks of nude rats. Intratumoral and intravenous injections of $^{111}$In labeled vectors are made. Quantitative biodistribution of modified compared to unmodified amplicon and virus is determined using scintography. GFP expression is also compared. Another set of tumor bearing animal groups is followed for tumor growth delay and treatment related sequelae, after modified and unmodified vector injections and ganciclovir administration.

EXAMPLE 3

The use of the Phage Display System to Select Tumor Selective Peptide Epitopes

For tumor selective receptors without naturally occurring small peptide ligands, phage display libraries provide an additional source of recombinant peptide sequences for targeting (Ladner, R. and Guterman, PCT patent publication WO 90/02809). In the phage display technique, nearly random oligonucleotide sequences are inserted into the filament binding protein of an E. coli filamentous phage (usually protein III of the M13 phage) to generate a library of phage expressing approximately $10^7$–$10^9$ different peptides. Phage that express a peptide sequence having high affinity for a specific molecule, cell, or tissue can then be selected out for expansion by selective binding and elution (O'Neil, K. and Hoess, R., Cur Opinion Struct Biol. 5: 443–449 (1995)).

Phage display, thus, provides a source of small, continuous peptide ligand epitope sequences that can be examined for targeting specificity and, therefore, for usefulness in a therapeutic gene therapy vector.

A mutant form of the epidermal growth factor (EGF) receptor, EGFRvIII, is selectively expressed in a high percentage of glioblastomas and a number of other malignancies, is more specific to tumors than the native form of EGFR (Wikstrand, C. J., et al., Cancer Research 55: 3140–3148 (1995)), and has been used as a target for therapeutic monoclonal antibodies (MAb) (Lorimer, I., et al., Proc Nat Acad Sci, USA 93: 14815–14820 (1996)).

Prostate-specific membrane antigen (PSMA) is a receptor, for which commercially available $^{111}$In labeled anti-PSMA MAb are available and used to image primary, recurrent and metastatic prostate tumors. PMSA may have a more widespread selective distribution on the neovasculature of other tumor types (Sodee, D. B., et al., Clinical Nuclear Medicine 21: 759–767 (1996); Liu, H., Cancer Research 57: 3629–3634 (1997)).

Figure 7:
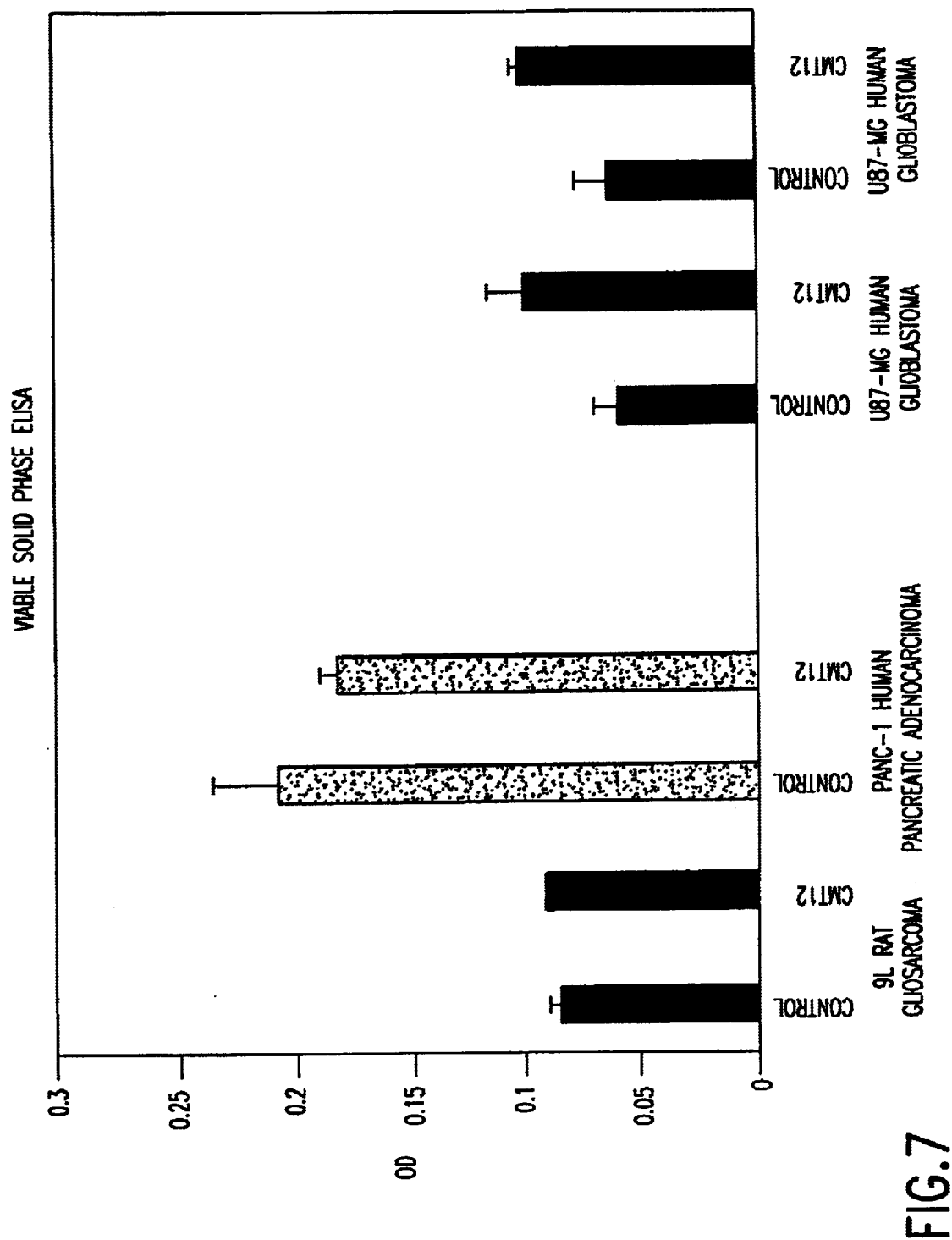
FIG. 7 is a bar graph showing the results of a viable solid phase (VSP) ELISA performed with bacteriophage CMT12, which was isolated by screening against U87 glioma cells. 9L rat glioblastoma (GBM) and PANC-1 cells were used as controls. Two independent experiments were carried out in triplicate.

In this example, phage were selected against the U87 human malignant glioma cell line. The binding and selectivity of the phage to glioma cells was examined using viable solid phase (VSP) ELISA (FIG. 7). Phage display libraries can also be selected against EGFRvIII, or against PSMA. Selected epitopes were evaluated for targeted binding in vitro using ELISA, or in vivo using $^{111}$In labeled phage in a murine tumor model.

Epitopes that demonstrate selectivity can be recombined into the gC HS binding domain of the HSV-1 amplicon vector of the present invention, and tested for targeting of infectivity in cell culture or in an animal tumor model. Useful epitopes can be evaluated for in vivo tumor imaging or targeting.

Methods and Results

Small peptide phage were selected from the CMTI library against viable U87-MG human malignant glioma cells using a viable fluid phase derivation of biopanning. The library, which initially contained phage expressing $2 \times 10^7$ different epitope sequences, collapsed after four rounds of selection such that 42% of recovered clones expressed a consensus sequence. Selective binding to U87 MG cells was subsequently demonstrated under physiological conditions at 152% (±14%) unselected phage using a viable solid phase (VSP) ELISA. In comparison, there was no difference in binding to control 9L rat gliosarcoma cells or PANC-1 human pancreatic adenocarcinoma cells. See, FIG. 7. Phage selected from a small peptide phage display library for specified binding can not only be used as gene transfer vectors, but the small peptide targeting epitopes can be sequenced and recombined into the attachment proteins of other viral vectors, or used by themselves to target therapeutic agents and diagnostic imaging radiolabels.

The specificity and binding characteristics of U87 selected phage display epitopes were evaluated by comparison to unselected phage for U87 cells, non-human glioma cells (9L), non-glial tumor cells (PANC-1), and non-malignant glia, using ELISA. Standard ELISA was performed by incubating the phage with fixed target and control cells, then using labeled anti-phage MIII coat protein MAb to quantify bound phage.

Phage display selection can be performed against plate-fixed EGFRvIII. Commercial phage display library (NEB) are added in DMEM with 10% FBS as a blocking agent, incubated, washed and eluted with urea (biopanning). Bound phage are recovered. ELISA will be performed as described above.

The present invention provides HSV-1 vectors that are selective beyond their intrinsic and previously designed selective toxicity for tumor cells. One ultimate objective is the inclusion of multiple targeting techniques in one or several vectors for use in combined modality therapy with complementary conventional therapies to obtain cures that have not yet been obtained, to lengthen survival time or improve quality of life of patients suffering from various pathologic conditions such as cancer, hemophilia, cystic fibrosis, muscular dystrophy, or other pathology having a genetic basis and, therefore, susceptible to treatment by gene therapy. Vector systems that improve a conventional treatment, for example, vector systems that create radiation therapy synergies to improve selectivity for tumors, can be particularly useful. Using the methods disclosed herein, the most selective and effective transgenes can be identified and introduced into a vector of the invention, then examined for efficacy in animal tumor models and for safety in primates. Human clinical trials subsequently can be initiated using combined modality regimens in subjects that failed conventional therapies.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A Herpes Simplex Virus (HSV) amplicon plasmid comprising:
   (a) an origin of replication,
   (b) a packaging sequence, and
   (c) a nucleotide sequence that encodes HSV glycoprotein C (gC) modified with a targeting domain;
wherein said HSV amplicon plasmid is capable of producing an HSV virion that is capable of targeting a target cell.

2. The HSV amplicon plasmid of claim 1, wherein said gC modified with a targeting domain is a modified gC lacking an HSBD and having a targeting domain in place of said HSBD.

3. The HSV amplicon plasmid of claim 2, further comprising a detectable marker gene.

4. The HSV amplicon plasmid of claim 3, wherein said detectable marker gene encodes green fluorescent protein (GFP); enhanced green fluorescent protein (EGFP), or beta galactosidase.

5. The HSV amplicon plasmid of claim 2, further comprising a gene for selection.

6. The HSV amplicon plasmid of claim 5, wherein said gene for selection is a gene for antibiotic resistance.

7. The HSV amplicon plasmid of claim 6, wherein said gene for antibiotic resistance is neomycin resistance (Neo$^R$).

8. A method of producing an HSV amplicon producer cell line comprising:
   (a) transfecting cells in culture with the HSV amplicon plasmid of claim 6, and
   (b) contacting the cells transfected according to step (a) with culture medium containing an appropriate antibiotic for selection; thereby producing an HSV amplicon producer cell line.

9. The method of claim 8, wherein said antibiotic is 418.

10. The HSV amplicon plasmid of claim 2, further comprising a transgene of interest.

11. The HSV amplicon plasmid of claim 1, wherein said HSV is HSV-1.

12. The HSV amplicon plasmid of claim 1, wherein said targeting domain renders said HSV virion, produced from said plasmid, capable of targeting a neoplastic cell.

13. The HSV amplicon plasmid of claim 12, further comprising a transgene of interest that encodes a gene product that is cytotoxic or cytostatic to neoplastic cells.

14. The HSV amplicon plasmid of claim 13, wherein said gene product that is cytotoxic to neoplastic cells is (a) a product capable of activating a chemotherapeutic agent; (b) a cytokine; (c) a tumor suppressor; or (d) a tumoricidal agent selected from the group consisting of diptheria toxin, pseudomonas toxin, an anti-angiogenesis gene product, a tumor vaccination gene product, a radiosensitivity gene product, antisense RNA, or a ribozyme.

15. The HSV amplicon plasmid of claim 1, wherein said targeting domain is IL-4, EGFRvIII, heregulin, DF3/MUC1, or prostate specific membrane antigen (PMSA).

16. The HSV amplicon plasmid of claim 1, wherein said targeting domain is a tumor selective epitope selected from a phage display library using phage display technology.

17. An HSV amplicon plasmid comprising:
    (a) an origin of replication,
    (b) a packaging sequence, and
    (c) a nucleotide sequence encoding a modified glycoprotein C (gC), wherein the nucleotide sequence that encodes the heparan sulfate binding domain (HSBD) of gC is flanked by at least two unique restriction sites that allow said nucleotide sequence that encodes the HSBD of gC to be replaced with a targeting domain sequence, thereby allowing said amplicon plasmid to produce an HSV virion that is capable of targeting a target cell.

18. An HSV amplicon plasmid comprising:
    (a) an origin of replication,
    (b) a packaging sequence, and
    (c) a nucleotide sequence encoding a modified gC, wherein the nucleotide sequence that encodes the HSBD of gC is replaced with a nucleotide sequence that encodes a labeling ligand comprising an amino acid sequence that can be used to facilitate purification or detection of an amplicon vector;
    wherein said HSV amplicon plasmid is capable of producing an HSV virion that can be traced or purified by contacting said labeling ligand with a compound or matrix that specifically interacts with said labeling ligand.

19. The HSV amplicon plasmid of claim 18, wherein said labeling ligand is a histidine tag.

20. A method of producing an HSV virion capable of targeting a target cell, said method comprising:
    (a) transfecting a suitable cell line with an HSV amplicon plasmid comprising:
        (i) an origin of replication, (ii) a packaging sequence, and (iii) a nucleotide sequence that encodes HSV glycoprotein C (gC) modified with a targeting domain; and
    (b) harvesting said HSV virion.

21. The method of claim 20, wherein said targeting domain renders said HSV virion, produced by said method, capable of targeting a neoplastic cell.

22. The method of claim 21, wherein said HSV amplicon plasmid further comprises a transgene of interest that encodes a gene product that is cytotoxic or cytostatic to neoplastic cells.

23. The method of claim 22, wherein said gene product that is cytotoxic to neoplastic cells is (a) a product capable of activating a chemotherapeutic agent; (b) a cytokine; (c) a tumor suppressor; or (d) a tumoricidal agent selected from the group consisting of diptheria toxin, pseudomonas toxin, an anti-angiogenesis gene product, a tumor vaccination gene product, a radiosensitivity gene product, antisense RNA, or a ribozyme.

24. A method of selectively targeting a neoplastic cell by administering to a patient the HSV virion produced by the method of claim 23.

25. A method of selectively targeting a neoplastic cell by administering to a patient the HSV virion produced by the method of claim 22.

26. The method of claim 21, wherein said HSV virion produced by said method is cytotoxic to neoplastic cells.

27. A method of selectively targeting a neoplastic cell by administering to a patient the HSV virion produced by the method of claim 26.

28. A method of selectively targeting a neoplastic cell by administering to a patient the patient the HSV virion produced by the method of claim 21.

29. The method of claim 28, wherein said neoplastic cell is derived from a central nervous system tumor.

30. The method of claim 28, wherein said neoplastic cell is derived form a breast cancer.

31. The method of claim 20, wherein said HSV amplicon plasmid is pCONGA4.

32. The method of claim 29, wherein said neoplastic cell is from a glioblastoma.

33. A method of selectively targeting a cell by administering to a patient the HSV virion produced by the method of claim 20.

34. The method of claim 20, further comprising packaging said HSV virion with an HSV helper virus.

35. The method of claim 20, further comprising packaging said HSV virion with a helper virus-free system.

36. The method of claim 34, wherein said HSV helper virus is replication defective or replication incompetent.

37. The method of claim 34, wherein said HSV helper virus has intrinsic cytotoxic properties.

38. The HSV-1 amplicon plasmid pCONGA.

39. The HSV-1 amplicon plasmid pCONGAH.

40. The HSV-1 amplicon plasmid pCONGA4.

* * * * *